(12) United States Patent
Hachtel et al.

(10) Patent No.: US 8,642,643 B2
(45) Date of Patent: *Feb. 4, 2014

(54) CXCR2 ANTAGONISTS

(75) Inventors: Stephanie Hachtel, Frankfurt (DE);
Juergen Dedio, Frankfurt (DE); Josef Pernerstorfer, Frankfurt (DE); Stephen Shimshock, Hillsbrough, NJ (US);
Carolina Lanter, Audubon, PA (US);
Raymond Kosley, Bridgewater, NJ (US)

(73) Assignee: Sanofi, Paris (FR)

( * ) Notice: Subject to any disclaimer, the term of this patent is extended or adjusted under 35 U.S.C. 154(b) by 909 days.

This patent is subject to a terminal disclaimer.

(21) Appl. No.: 12/337,970

(22) Filed: Dec. 18, 2008

(65) Prior Publication Data

US 2009/0258906 A1    Oct. 15, 2009

Related U.S. Application Data

(63) Continuation of application No. PCT/EP2007/005575, filed on Jun. 25, 2007.

(30) Foreign Application Priority Data

Jun. 28, 2006   (EP) ..................... 06013321

(51) Int. Cl.
| | |
|---|---|
| *A01N 43/02* | (2006.01) |
| *A61K 31/38* | (2006.01) |
| *A01N 43/12* | (2006.01) |
| *A01N 43/40* | (2006.01) |
| *A61K 31/44* | (2006.01) |
| *C07D 333/00* | (2006.01) |
| *C07D 409/02* | (2006.01) |
| *C07D 409/00* | (2006.01) |
| *C07D 411/00* | (2006.01) |

(52) U.S. Cl.
USPC ............ 514/430; 514/443; 514/337; 549/49; 546/281.1

(58) Field of Classification Search
USPC .......... 514/430, 443, 337; 549/49; 546/281.1
See application file for complete search history.

(56) References Cited

U.S. PATENT DOCUMENTS

| | | | |
|---|---|---|---|
| 4,962,224 | A | 10/1990 | Wrobel et al. |
| 4,994,477 | A | 2/1991 | Kempf et al. |
| 7,919,628 | B2 | 4/2011 | Hachtel et al. |
| 2002/0123522 | A1 | 9/2002 | Fritz et al. |
| 2004/0204417 | A1 | 10/2004 | Perez et al. |
| 2005/0059705 | A1 | 3/2005 | Mjalli et al. |
| 2008/0090854 | A1 | 4/2008 | Hachtel et al. |

FOREIGN PATENT DOCUMENTS

| | | |
|---|---|---|
| EP | 1676834 | 7/2006 |
| FR | 2825706 | 12/2002 |
| WF | WO2005/023818 | 3/2005 |
| WO | WO 99/07351 | 2/1999 |
| WO | WO01/58852 | 8/2001 |
| WO | WO2004/108681 | 12/2004 |
| WO | WO2005/033102 | 4/2005 |
| WO | WO2005/051940 | 6/2005 |
| WO | WO2005/070906 | 8/2005 |
| WO | WO2006/040646 | 4/2006 |
| WO | WO2006/052722 | 5/2006 |
| WO | WO2006/099610 | 9/2006 |

OTHER PUBLICATIONS

Boschelli D.H. et al., "Inhibition of E-Selectin-, ICAM-1-, and VCAM-1-Mediated Cell Adhesion by Benzo[b]thiophene-, Benzofuran-, Indole-, and Naphthalene-2-Carboxamides: Identification of PD 144795 as an Antiinflammatory Agent", *Journal of Medicinal Chemistry*, 38:4597-4614 (1995).

International Search Report dated Mar. 29, 2006 corresponding to International Application No. PCT/EP2005/013624 from related U.S. Appl. No. 13/079,522.

U.S. Office Action dated Nov. 18, 2011 received in related U.S. Appl. No. 13/079,522.

Kubinyi H., "3D QSAR in Drug Design: Ligand-Protein Interactions and Molecular Similarity", vol. 2-3, Springer, 1998, 800 pages, pp. 243-244 provided.

Wermuth, The Practice of Medicinal Chemistry, 2d ed., 768 pages, Chapters 9-10 provided, 2003.

International Search Report dated Oct. 2, 2007 corresponding to International Application No. PCT/EP2007/005576 from related U.S. Appl. No. 12/337,040.

U.S. Office Action dated Jan. 12, 2012 received in related U.S. Appl. No. 12/337,040.

(Continued)

*Primary Examiner* — Samira Jean-Louis
(74) *Attorney, Agent, or Firm* — Scully, Scott, Murphy & Presser, P.C.

(57) ABSTRACT

The invention relates to compounds of the formula I

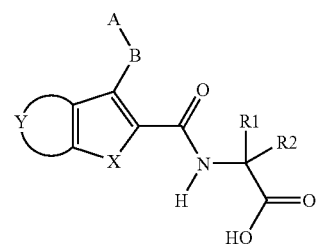

in which R1, R2, A, B, X and Y have the meanings indicated in the claims, and/or a pharmaceutically acceptable salt and/or a prodrug thereof. Because of their properties as inhibitors of chemokine receptors, especially as CXCR2 inhibitors, the compounds of the formula I and the pharmaceutically acceptable salts and prodrugs thereof are suitable for the prevention and treatment of chemokine mediated diseases.

12 Claims, No Drawings

(56) References Cited

OTHER PUBLICATIONS

Jodlbauer J. et al., "Towards Ochratoxin a Selective Molecularly Imprinted Polymers for Solid-Phase Extraction", *Journal of Chromatography A*, 945(1-2):45-63 (2002).

U.S. Office Action dated Sep. 26, 2011 received in related U.S. Appl. No. 12/337,040.

Van den Eynde et al., Database Caplus Chemical Abstracts Service, Columbus, Ohio, US; Database Accession No. 1972:47393, Abstract, DE 2108189, Sep. 9, 1971.

International Search Report dated Sep. 14, 2007 corresponding to International Application No. PCT/EP2007/005574 from related U.S. Appl. No. 12/337,107.

U.S. Final Office Action dated Feb. 29, 2012 received in related U.S. Appl. No. 12/337,107.

Huff J.R., "HIV Protease: A Novel Chemotherapeutic Target for AIDS", *Journal of Medicinal Chemistry*, 34(8):2305-2314 (Aug. 1991).

The Merck Manual of Diagnosis and Therapy (16$^{th}$ Ed., pp. 52-55) (1999).

Johnson J. et al., "Relationships Between Drug Activity in NCI Preclinical In Vitro and In Vivo Models and Early Clinical Trials", *British Journal of Cancer*, 84(10):1424-1431 (2001).

Lala P.K. et al., "Role of Nitric Oxide in Tumor Progression: Lessons from Experimental Tumors", *Cancer and Metastasis Reviews*, 17:91-106 (1998).

Sausville E.A. et al., "Contributions of Human Tumor Xenografts to Anticancer Drug Development", *Cancer Research* 66(7):3351-3354 (Apr. 1, 2006).

Golub T.R. et al., "Molecular Classification of Cancer: Class Discovery and Class Prediction by Gene Expression Monitoring", *Science*, 286:531-537 (1999).

U.S. Office Action dated Jul. 12, 2011 received in related U.S. Appl. No. 12/337,107.

International Search Report dated Sep. 3, 2007 corresponding to International Application No. PCT/EP2007/005575.

International Search Report dated Sep. 3, 2007 corresponding to International Application No. PCT/EP2007/005577 from related U.S. Appl. No. 12/337,980.

U.S. Final Office Action dated Mar. 22, 2012 received in related U.S. Appl. No. 12/337,980.

U.S. Office Action dated Nov. 2, 2011 received in related U.S. Appl. No. 12/337,980.

CXCR2 ANTAGONISTS

Chemokines are a family of low molecular weight proteins (8-13 kDa) that are classified into four distinct groups depending on the positioning of the cysteine motif at the amino terminus. The family members comprise CXC, CC, XC, and CX3C chemokines of which CXC and CC are the largest and most characterized. The CXC chemokines include interleukin-8 (IL-8), neutrophil-activating protein-2 (NAP-2), growth-related oncogenes GRO-α, GRO-β, GRO-γ, epithelial cell-derived neutrophil activating factor-78 (ENA-78), granulocyte chemoattractant protein-2 (GCP-2), γ-interferon-inducible protein-10 (γIP-10), interferon-inducible T cell α-chemoattractant (I-TAC), monokine induced by γ-interferon (Mig) and platelet factor-4 (PF-4). CC chemokines include RANTES (regulated on activation normal T cell expressed and secreted), macrophage inflammatory proteins MIP-1α, MIP-1β, monocyte chemoattractant proteins MCP-1, MCP-2, MCP-3 and eotaxin. The XC family comprises two members, lymphotactin-α and lymphotactin-β, and the CX3C family consists only of a single chemokine named fractalkine (Murphy et al., Pharmacol. Rev. 52: 145-176, 2000).

Chemokines mediate their biological effects by binding to cell surface molecules, which belong to the superfamily of seven-transmembrane spanning receptors that signal through coupling to heterotrimeric G proteins. Although most chemokine receptors recognize more than one chemokine, they are almost always restricted to a single subclass. Chemokine receptor binding initiates a cascade of intracellular events of which the first step is the binding of the receptor by its high-affinity ligand. This induces a conformational change leading to a dissociation of the receptor-associated heterotrimeric G proteins into α and βγ subunits. These G protein subunits are able to activate various effector proteins, including phospholipases leading to generation of inositol trisphosphate, an increase in cytosolic calcium, and activation of protein kinases. This cascade of intracellular events mediates a wide range of functions in different leukocytes such as chemotaxis, degranulation, oxidative burst, phagocytosis, and lipid mediator synthesis.

Interleukin-8 (IL-8) is a key mediator of immunological reactions in inflammatory disorders such as atherosclerosis, ischemia/reperfusion injury, rheumatoid arthritis, chronic obstructive pulmonary disease, respiratory distress syndrome, asthma, cystic fibrosis, and psoriasis (Bizarri et al., Curr. Med. Chem. 2: 67-79, 2003). IL-8 is the most characterized member of the CXC subfamily of chemokines. Leukocyte responses to IL-8 are mediated via specific cell surface receptors, CXCR1 and CXCR2. Whereas CXCR1 is selectively activated by IL-8, CXCR2 responds to several additional chemokines including growth-related oncogenes GRO-α, GRO-β, GRO-γ, neutrophil-activating protein-2 (NAP-2), epithelial cell-derived neutrophil activating factor-78 (ENA-78), and granulocyte chemoattractant protein-2 (GCP-2). The common denominator shared by all chemokines that activate CXCR2 is a Glu-Leu-Arg (ELR) sequence in the amino terminus, which appears to serve as a recognition sequence for receptor binding and activation (Herbert et al., J. Biol. Chem. 266: 18989-18994, 1991).

Early investigations concentrated on the effect of IL-8 on neutrophils, which respond to IL-8 with calcium mobilization, actin polymerization, enzyme release, chemotaxis, and the respiratory burst. Despite similar affinities for IL-8 and similar receptor numbers of CXCR1 and CXCR2 on neutrophils, both receptors are functionally different. Responses such as calcium mobilization and the release of granule enzymes are mediated through both receptors, whereas the respiratory burst and the activation of phospholipase D depend exclusively on stimulation of CXCR1 (Jones et al., Proc. Natl. Acad. Sci. USA 93: 6682-6686, 1996). Due to their prominent role in neutrophil recruitment, CXCR1 and CXCR2 are thought to be important in several acute neutrophil-mediated diseases such as acute respiratory distress syndrome and ischemia/reperfusion injuries, as well as in chronic diseases such as asthma, psoriasis, dermatitis, and arthritis.

It has been shown that CXCR2 is also expressed by monocytes. Despite IL-8's inactivity in monocyte chemotaxis assay, this factor induces calcium flux and respiratory burst in monocytes and enhances adhesion of monocytes in static assays. Similarly, GRO-α enhances adhesion of monocytes to stimulated endothelial cells. Moreover, IL-8 is able to induce firm arrest of monocytes on endothelial cells under conditions of physiological flow (Gerszten et al., Nature 398: 718-723, 1999). Since CXCR2 is strongly expressed on monocytes and macrophages in atherosclerotic lesions where it is suggested to play a key role in chemoattraction, retension, expansion, and activation of monocytes and macrophages, this strongly suggests that CXCR2 and one or more of its ligands (IL-8, GRO-α) play a pathophysiological role in atherosclerosis (Huo et al., J. Clin. Invest. 108: 1307-1314, 2001).

Apart from neutrophils and monocytes, numerous cell types have been shown to express IL-8 receptors. These cell types include neurons, various cancer cells, keratinocytes, and endothelial cells. Several lines of evidence indicate that IL-8 plays a direct role in angiogenesis via stimulation of CXCR2 expressed on endothelial cells. IL-8 has been shown to bind specifically to endothelial cells and induce chemotaxis. IL-8 is able to induce neovascularization in the absence of inflammatory responses (Koche et al., Science 258: 1798-1801, 1992). Moreover, there is accumulating evidence that IL-8 could play a key role in melanoma progression and metastasis as patients with melanoma metastases have elevated serum levels of IL-8. IL-8 is supposed to act as an autocrine growth and metastatic factor for melanoma cells (Schadendorf et al., J. Immunol: 151-157, 1993).

Due to the wide range of actions of IL-8, such as attraction and activation of neutrophils and monocytes/macrophages as well as promotion of endothelial cell proliferation and cancer cell growth, the inhibition of chemokine receptors CXCR1 and CXCR2 is expected to be beneficial in the prevention and treatment of numerous diseases. Besides acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases include adult respiratory distress syndrome, inflammatory bowel disease, ulcerative colitis, Crohn's disease, atopic dermatitis, cystic fibrosis, psoriasis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

WO 2005/033102 (Amphora Discovery) relates to thiophene derivatives as inhibitors for ATP-utilizing enzymes. WO 2006/040646 (Pfizer) describes Benzimidazole or Indole amides useful in the treatment of abnormal cell growth, in particular cancer. WO 2005/051940 (Lilly Co) discloses phenyl-benzothiophene derivatives of formula (IA) useful as modulators for the vitamin D receptor having different substituents on the phenyl-benzothiophene. WO 2006/052722 (Smithkline Beecham) relates to mono or bicyclic amide derivatives of formula (I) useful as inhibitors of glycogen phosphorylase having a different connecting group and substitution pattern at the condensed ring system. EP 1676834 (Sanofi-Aventis) describes fused aromatic compounds which are different from the present non-aromatic carboxamides derivatives. WO 01/58852 (Dompe) describes N-(2-aryl-propionyl)amides of formula (I) useful in the inhibition of neutrophils induced by Il-8.

The invention provides novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

The invention relates to a compound of formula I

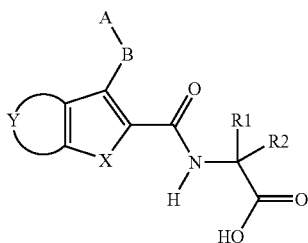

wherein
X is —CR3=CR4-, —CR5=N—, —N=CR6-, —NR7- or —S—;
R3, R4, R5 and R6
  are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, S(O)$_o$R32, S(O)$_p$NR33R34, aryl, heteroaryl, arylalkyl with alkyl having 1, 2, 3 or 4 carbon atoms or heteroarylalkyl with alkyl having 1, 2, 3 or 4 carbon atoms;
  R27 is hydrogen or alkyl having 1, 2, 3 or 4 carbon atoms;
  R28 is hydrogen, alkyl having 1, 2, 3 or 4 carbon atoms, aryl, C(O)H, C(O)alkyl with alkyl having 1, 2, 3 or 4 carbon atoms or C(O)aryl;
  R29 is hydrogen, OH, alkyl with 1, 2, 3 or 4 carbon atoms, alkoxy with 1, 2, 3 or 4 carbon atoms or aryl;
  R30, R31, R33 and R34
    are, independently of one another, hydrogen, alkyl having 1, 2, 3 or 4 carbon atoms or aryl;
  R32 is OH, alkyl having 1, 2, 3 or 4 carbon atoms, alkoxy with 1, 2, 3 or 4 carbon atoms or aryl;
  o and p
    are, independently of one another, 1 or 2;
R7 is hydrogen, alkyl having 1, 2, 3 or 4 carbon atoms or C(O)R35;
R35 is hydrogen, alkyl with 1, 2, 3 or 4 carbon atoms or aryl;
Y is —C(R61R62)-C(R61R62)-C(R61R62)-,
  —S(O)$_u$—C(R63R64)-C(R61R62)-,
  —C(R63R64)-S(O)$_u$—C(R63R64)-,
  —C(R61R62)-C(R63R64)-S(O)$_u$—
  —C(R61R62)-C(R61R62)-C(R61R62)-C(R61R62)-,
  —S(O)$_u$—C(R63R64)-C(R61R62)-C(R61R62)-,
  —C(R63R64)-S(O)$_u$—C(R63R64)-C(R61R62)-,
  —C(R61R62)-C(R63R64)-S(O)$_u$—C(R63R64)-,
  —C(R61R62)-C(R61R62)-C(R63R64)-S(O)$_u$—,
  —S(O)$_u$—C(R63R64)-C(R63R64)-S(O)$_u$—,
  —S(O)$_v$—CR65=CR66- or
  —CR67=CR68-S(O)$_v$—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;
R62, R63 and R64
  are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68
  are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$;

u is 0, 1 or 2;
v is 0, 1 or 2;
A is cycloalkyl having 3, 4, 5, 6, 7 or 8 carbon atoms, heterocycle, aryl or heteroaryl;
  in which the cycloalkyl or heterocycle radical can be condensed to an aryl or heteroaryl radical and in which the cycloalkyl or heterocycle radical and the optionally condensed aryl or heteroaryl radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)_sR47$, $S(O)_tNR48R49$, $—(CH_2)_k$-aryl or $—(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a—(CH_2)_b—(CF_2)_c—CF_3$;
R9 is hydrogen or alkyl having 1, 2, 3 or 4 carbon atoms;
R10 is hydrogen, alkyl having 1, 2, 3 or 4 carbon atoms, aryl, C(O)H, C(O)alkyl having 1, 2, 3 or 4 carbon atoms or C(O)aryl;
R44 is hydrogen, OH, alkyl with 1, 2, 3 or 4 carbon atoms, alkoxy with 1, 2, 3 or 4 carbon atoms, cycloalkyl having 3, 4, 5 or 6 carbon atoms or aryl;
R45, R46, R48 and R49 are, independently of one another, hydrogen, alkyl having 1, 2, 3 or 4 carbon atoms or aryl;
R47 is OH, alkyl having 1, 2, 3 or 4 carbon atoms, alkoxy with 1, 2, 3 or 4 carbon atoms or aryl;
a is zero or 1;
b, c, k and l
  are, independently of one another, zero, 1, 2 or 3;
s and t
  are, independently of one another, 1 or 2;
in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)SR47$, $S(O)_tNR48R49$, $—(CH_2)_k$-aryl or $—(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a—(CH_2)_b—(CF_2)_c—CF_3$;
R9 is hydrogen or alkyl having 1, 2, 3 or 4 carbon atoms;
R10 is hydrogen, alkyl having 1, 2, 3 or 4 carbon atoms, aryl, C(O)H, C(O)alkyl having 1, 2, 3 or 4 carbon atoms or C(O)aryl;
R44 is hydrogen, OH, alkyl with 1, 2, 3 or 4 carbon atoms, alkoxy with 1, 2, 3 or 4 carbon atoms, cycloalkyl having 3, 4, 5 or 6 carbon atoms or aryl;
R45, R46, R48 and R49
  are, independently of one another, hydrogen, alkyl having 1, 2, 3 or 4 carbon atoms or aryl;
R47 is OH, alkyl having 1, 2, 3 or 4 carbon atoms, alkoxy with 1, 2, 3 or 4 carbon atoms or aryl;
a is zero or 1;
b, c, k and l
  are, independently of one another, zero, 1, 2 or 3;
s and t
  are, independently of one another, 1 or 2;
B is —O—C(R11R12)-, —C(R50R51)-O—, —C≡C—, —CR52=CR53-, —C(R13R14)-C(R15R16)-, —NR17-C(R18R19)-, —C(R54R55)-NR56-, —NR20-C(O)— or —C(O)—NR57—;
R11, R12, R13, R14, R15, R16, R17, R18, R19, R20, R50, R51, R52, R53, R54, R55, R56 and R57
  are, independently of one another, hydrogen or alkyl having 1, 2, 3 or 4 carbon atoms, in which 1, 2, 3, 4, 5, 6, 7, 8 or 9 hydrogen atoms may be substituted by fluorine atoms;
R1 is hydrogen or alkyl having 1, 2, 3, 4, 5 or 6 carbon atoms;
  which can be unsubstituted or substituted by 1, 2, 3, 4 or 5 radicals selected from the group consisting of F, Cl, Br, I, $—O_i—(CH_2)_j—R25$;
  i is 0 or 1;
  j is 0, 1, 2 or 3;
  R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;
R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4 5, 6, 7 or 8 atoms;
  wherein alkyl is unsubstituted or substituted by 1, 2, 3, 4 or 5 radicals selected from the group consisting of F, Cl, Br, I, $—O_m—(CH_2)_n—R26$;
  m is 0, or 1;
  n is 0, 1, 2 or 3;
  R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2, or 3 radicals selected from F, Cl, Br or I;
  and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

or

R1 and R2
form, together with the carbon atom to which they are attached, a 3-, 4-, 5- or 6-membered carbon ring, wherein one carbon atom, which is not adjacent to the carbon atom, to which R1 and R2 are attached, can be replaced by —O—, —NR58- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;
wherein the formed ring and the condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$, SCF$_3$, SF$_5$, or alkyl having 1, 2, 3 or 4 carbon atoms;

R58 is hydrogen, alkyl having 1, 2, 3 or 4 carbon atoms or C(O)R59;
R59 is hydrogen, alkyl with 1, 2, 3 or 4 carbon atoms or phenyl;
w is 0, 1 or 2;

and/or a pharmaceutically acceptable salt and/or a prodrug thereof.

Preference is given to a compound of the formula I, in which:

X is —CR3=CR4-, —CR5=N—, —N=CR6-, —NR7- or —S—;
R3, R4, R5 and R6
are, independently of one another, hydrogen, F, Cl, Br, I, alkyl having 1, 2, 3 or 4 carbon atoms or alkoxy having 1, 2, 3 or 4 carbon atoms;
R7 is hydrogen or alkyl having 1, 2, 3 or 4 carbon atoms;
Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—,
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or SCF$_3$;

R62, R63 and R64
are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;

R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, NO$_2$, CN or SCF$_3$;

A is cycloalkyl having 3, 4, 5, 6, 7 or 8 carbon atoms, heterocycle, aryl or heteroaryl;
in which the cycloalkyl or heterocycle radical can be condensed to an aryl radical and in which the cycloalkyl or heterocycle radical is unsubstituted or substituted by 1, 2 or 3 radicals selected from the group consisting of F, Cl, Br, I or alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms;
in which the aryl or heteroaryl radical can be condensed to an cycloalkyl or heterocycle radical and in which the aryl or heteroaryl radical is unsubstituted or substituted by 1, 2, 3 or 4 radicals selected from the group consisting of F, Cl, Br, I, CN, NO$_2$, SF$_5$, —NR9R10, alkoxy having 1, 2, 3 or 4 carbon atoms, alkyl having 1, 2, 3, 4, 5 or 6 carbon atoms, —O$_a$—(CH$_2$)$_b$—(CF$_2$)$_c$—CF$_3$, —O$_d$—CHF$_2$, —O$_e$—CH$_2$F, —SO$_f$-alkyl having 1, 2, 3 or 4 carbon atoms, S—(CH$_2$)$_g$—(CF$_2$)$_h$—CF$_3$, —(CH$_2$)$_k$-aryl or —(CH$_2$)$_l$-heteroaryl, in which the aryl and heteroaryl radicals can be substituted by F, Cl, Br, I, CF$_3$, alkoxy having 1, 2, 3 or 4 carbon atoms or alkyl having 1, 2, 3 or 4 carbon atoms;
R9 and R10
are, independently of one another, hydrogen or alkyl having 1, 2, 3 or 4 carbon atoms;

a, d and e
   are, independently of one another, zero or 1;
b, c, g, h, k and l
   are, independently of one another, zero, 1, 2 or 3;
f is zero, 1 or 2;
B is —O—(CR11R12)-, —C≡C—, —C(R13R14)-C(R15R16)-, —NR17-C(R18R19)- or —NR20-C(O)—;
R11, R12, R13, R14, R15, R16, R17, R18, R19 and R20
   are, independently of one another, hydrogen or alkyl having 1, 2, 3 or 4 carbon atoms;
R1 is hydrogen or alkyl having 1, 2, 3, 4, 5 or 6 carbon atoms; and
R2 is alkyl having 1, 2, 3, 4, 5 or 6 carbon atoms or phenyl,
   wherein alkyl is unsubstituted or substituted by 1, 2, 3, 4 or 5 radicals selected from the group consisting of F, Cl, Br, I, —$O_m$—$(CH_2)_n$—R26;
   m is 0, or 1;
   n is 0, 1, 2 or 3;
   R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms;
      in which the phenyl, heteroaryl, cycloalkyl or heterocyclyl are unsubstituted or substituted by 1, 2, or 3 radicals selected from F, Cl, Br or I;
or
R1 and R2
   form, together with the carbon atom to which they are attached, a 3-, 4, 5- or 6-membered saturated or partly saturated carbon ring, which can be condensed to phenyl;
or
R1 and R2
   form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NH— or —S—;
and/or a pharmaceutically acceptable salt and/or prodrug thereof.

Particular preference is given to a compound of the formula I in which:
X is —CR3=CR4-, —CR5=N—, —N=CR6-, —NH— or —S—;
   R3, R4, R5 and R6
      are, independently of one another, hydrogen, F, Cl, Br or alkyl having 1, 2, 3, or 4 carbon atoms; preferably R3, R4, R5 and R6 are, independently of one another, hydrogen, F, Cl or Br;
Y is —C(R61R62)-C(R61R62)-C(R61R62)-,
   —S—C(R63R64)-C(R61R62)-,
   —C(R63R64)-S—C(R63R64)-,
   —C(R61R62)-C(R63R64)-S—
   —C(R61R62)-C(R61R62)-C(R61R62)-C(R61R62)-,
   —S—C(R63R64)-C(R61R62)-C(R61R62)-,
   —C(R63R64)-S—C(R63R64)-C(R61R62)-,
   —C(R61R62)-C(R63R64)-S—C(R63R64)-,
   —C(R61R62)-C(R61R62)-C(R63R64)-S—,
   —S—C(R63R64)-C(R63R64)-S—,
   —S—CR65=CR66- or
   —CR67=CR68-S—;
   R61, R62, R63 and R64
      are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
      with the proviso, that in any embodiment of Y a maximum of 4 of the substituents R61 to R64 are not hydrogen;
   R65, R66, R67 and R68
      are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
A is cyclohexyl or an aryl or heteroaryl radical selected from phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl or quinolyl;
   in which the cyclohexyl is unsubstituted or substituted by 1, 2 or 3 radicals selected from the group consisting of F or alkyl having 1, 2, 3 or 4 carbon atoms;
   in which the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, —$CF_3$, —$OCF_3$, —$OCH_2CF_3$, —$OCHF_2$, —$SCH_3$—, —$SOCH_3$, —$SO_2CH_3$, —$SCF_3$, phenyl or benzyl;
   wherein phenyl can be substituted by Cl;
B is —O—C(R11R12)-; —C≡C—, or —C(R13R14)-C(R15R16)-;
   R11, R13, R14, R15 and R16
      are hydrogen;
   R12 is hydrogen or methyl;
R1 is alkyl having 1, 2, 3 or 4 carbon atoms;
and
R2 is alkyl having 1, 2, 3 or 4 carbon atoms, phenyl or benzyl;
or
R1 and R2
   form, together with the carbon atom to which they are attached, a cyclopropane, cyclobutane, cyclopentane, cyclohexane, cyclopentene ring or indene;
or
R1 and R2
   form, together with the carbon atom to which they are attached, a tetrahydro-thiophene or tetrahydro-thiopyrane ring;
and/or a pharmaceutically acceptable salt and/or prodrug thereof.

Special preference is given to a compound of the formula I, in which
X is —CR3=CR4- or —S—;
   R3 and R4
      are, independently of one another, hydrogen, F, Cl, Br or alkyl having 1, 2, 3, or 4 carbon atoms; preferably R3, R4, R5 and R6 are, independently of one another, hydrogen, F, Cl or Br;
Y is —C(R61R62)-C(R61R62)-C(R61R62)-,
   —C(R61R62)-C(R61R62)-C(R61R62)-C(R61R62)-,
   —S—CR65=CR66- or
   —CR67=CR68-S—;
   R61 and R62
      are, independently of one another, hydrogen, F or alkyl having 1, 2, 3 or 4 carbon atoms;
      with the proviso, that in any embodiment of Y a maximum of 4 of the substituents R61 to R62 are not hydrogen;

R65, R66, R67 and R68
    are, independently of one another, hydrogen, F, Cl, Br, I, alkyl having 1, 2, 3 or 4 carbon atoms;
A is cyclohexyl or an aryl or heteroaryl radical selected from phenyl, naphthyl, indanyl, thienyl, pyridyl, thiazolyl, pyrazinyl, pyrimidinyl, pyridazinyl, benzothiophenyl, benzothiazolyl or quinolyl;
    wherein cyclohexyl is unsubstituted or substituted by 1, 2 or 3 radicals selected from the group consisting of F or alkyl having 1, 2, 3 or 4 carbon atoms;
    and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl;
B is —O—C(R11R12)-;
R11 is hydrogen;
R12 is hydrogen or methyl;
R1 is methyl or ethyl;
and
R2 is methyl or ethyl;
or
R1 and R2
    form, together with the carbon atom to which they are attached, a cyclobutane or cyclopentane ring;
and/or a pharmaceutically acceptable salt and/or a prodrug thereof.

More special preference is given to a compound of the formula I, in which
X is —CR3=CR4-
    R3 and R4
        are, independently of one another, hydrogen, F or methyl;
Y is —C(R61R62)-C(R61R62)-C(R61R62)- or
    —C(R61R62)-C(R61R62)-C(R61R62)-C(R61R62)-;
    R61 and R62 are, independently of one another, hydrogen or F; with the proviso, that in any embodiment of Y a maximum of 4 of the substituents R61 to R62 are not hydrogen;
A is phenyl, pyridyl or benzothiazolyl;
    which is unsubstituted or substituted by F, $CF_3$ or $OCF_3$;
B is —O—$CH_2$—;
R1 is methyl;
and
R2 is methyl or ethyl;
and/or a pharmaceutically acceptable salt and/or a prodrug thereof.

Most special preference is given to a compound of the formula I, in which
X is —CR3=CR4-
    R3 and R4
        are, independently of one another, hydrogen or F;
Y is —C(R61R62)-C(R61R62)-C(R61R62)-C(R61R62)-;
    R61 and R62 are, independently of one another, hydrogen or F; with the proviso, that in any embodiment of Y a maximum of 4 of the substituents R61 to R62 are not hydrogen;
A is phenyl, pyridyl or benzothiazolyl;
    which is unsubstituted or substituted by F, $CF_3$ or $OCF_3$;
B is —O—$CH_2$—;
R1 is methyl;
and
R2 is methyl or ethyl;
and/or a pharmaceutically acceptable salt and/or a prodrug thereof.

In one embodiment X in compounds of formula I is described by —CR3=CR4-, —CR5=N—, —N=CR6-, —NR7- or —S—, wherein R3, R4, R5 and R6 are independently of one another, hydrogen, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen; preference is given to compounds, in which X is described by —CR3=CR4-, —CR5=N—, —N=CR6-, —NH— or —S—, wherein R3, R4, R5 and R6 are, independently of one another, hydrogen, F, Cl, Br, I or alkyl having 1, 2, 3 or 4 carbon atoms, preferably R3, R4, R5 and R6 are, independently of one another, hydrogen, F, Cl, Br or alkyl having 1, 2, 3, or 4 carbon atoms, preferably hydrogen, F, Cl or Br; particular preference is given to compounds, in which X is described as —CR3=CH—, —CH=N—, —N=CH, NH or —S—, wherein R3 is defined as hydrogen, F, Cl, Br or alkyl having 1, 2, 3, or 4 carbon atoms, preferably hydrogen, F, Cl or Br; more particular preference is given to compounds, in which X is described as —CR3=CH— or —S—, wherein R3 is defined as hydrogen, F, Cl or Br.;
most particular preference is given to compounds, in which X is described as —CR3=CH—, wherein R3 is defined as hydrogen, F or methyl, preferably as hydrogen or F.
X is attached with its left hand side to the carbon atom being directly connected to the Y-ring and with its right hand side to the other carbon atom.

In a further embodiment of compounds of formula I
Y is —C(R61R62)-C(R61R62)-C(R61R62)-,
    —S—C(R63R64)-C(R61R62)-,
    —C(R63R64)-S—C(R63R64)-,
    —C(R61R62)-C(R63R64)-S—
    —C(R61R62)-C(R61R62)-C(R61R62)-C(R61R62)-,
    —S—C(R63R64)-C(R61R62)-C(R61R62)-,
    —C(R63R64)-S—C(R63R64)-C(R61R62)-,
    —C(R61R62)-C(R63R64)-S—C(R63R64)-,
    —C(R61R62)-C(R61R62)-C(R63R64)-S—,
    —S—C(R63R64)-C(R63R64)-S—,
    —S—CR65=CR66- or
    —CR67=CR68-S—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;
R62, R63 and R64
    are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso, that in any embodiment of Y a maximum of 4 of the substituents R61 to R64 are not hydrogen;

R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$.

In a preferred embodiment of compounds of formula I
Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;

R61, R62, R63 and R64
are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
with the proviso, that in any embodiment of Y a maximum of 4 of the substituents R61 to R64 are not hydrogen;

R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

In a more preferred embodiment of compounds of formula I
Y is —C(R61R62)-C(R61R62)-C(R61R62)-,
—C(R61R62)-C(R61R62)-C(R61R62)-C(R61R62)-,
—S—CR65=CR66- or
—CR67=CR68-S—;

R61 and R62
are, independently of one another, hydrogen, F or alkyl having 1, 2, 3 or 4 carbon atoms;
with the proviso, that in any embodiment of Y a maximum of 4 of the substituents R61 to R62 are not hydrogen;

preferably, R61 and R62
are, independently of one another, hydrogen or F;
with the proviso, that in any embodiment of Y a maximum of 4 of the substituents R61 to R62 are not hydrogen;
more preferably, R61 and R62 are hydrogen;

R65, R66, R67 and R68
are, independently of one another, hydrogen, F, Cl, Br or alkyl having 1, 2, 3 or 4 carbon atoms;
preferably R65, R66, R67 and R68
are, independently of one another, hydrogen or F;
more preferably, hydrogen.

In a most preferred embodiment of compounds of formula I
Y is —C(R61R62)-C(R61R62)-C(R61R62)-C(R61R62)-,
R61 and R62
are, independently of one another, hydrogen, F or alkyl having 1, 2, 3 or 4 carbon atoms;
with the proviso, that in any embodiment of Y a maximum of 4 of the substituents R61 to R62 are not hydrogen;
preferably R61 and R62
are, independently of one another, hydrogen or F;
with the proviso, that in any embodiment of Y a maximum of 4 of the substituents R61 to R62 are not hydrogen;
more preferably, Y is —$CH_2$—$CH_2$—$CH_2$—$CH_2$—.

Y is attached with its right hand side to the carbon atom connected to X and with its left hand side to the other carbon atom.

In a further embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is unsubstituted or substituted by 1, 2 or 3 radicals selected from the group consisting of F, Cl, Br, I, alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms and wherein the aryl or heteroaryl radical can be condensed to an cycloalkyl or heterocycle radical and wherein the aryl or heteroaryl radical is unsubstituted or substituted by 1, 2, 3 or 4 radicals selected from the group consisting of F, Cl, Br, I, CN, $NO_2$, $SF_5$, —NR9R10, alkoxy having 1, 2, 3 or 4 carbon atoms, alkyl having 1, 2, 3, 4, 5 or 6 carbon atoms, —$O_a$—$(CH_2)_b$—$(CF_2)_c$—$CF_3$, —$O_d$—$CHF_2$, —$O_e$—$CH_2F$, —$SO_f$-alkyl having 1, 2, 3 or 4 carbon atoms, S—$(CH_2)_g$—$(CF_2)_h$—$CF_3$, —$(CH_2)_k$-aryl or —$(CH_2)_l$-heteroaryl, in which the aryl and heteroaryl radicals can be substituted by F, Cl, Br, I, alkoxy having 1, 2, 3 or 4 carbon atoms or alkyl having 1, 2, 3 or 4 carbon atoms, wherein R9 and R10 are, independently of one another, hydrogen or alkyl having 1, 2, 3 or 4 carbon atoms, a, d and e are, independently of one another, zero or 1, b, c, g, h, k and l are, independently of one another, zero, 1, 2 or 3 and f is zero, 1 or 2.

Preference is given to compounds, wherein A is described by cyclohexyl or an aryl or heteroaryl radical selected from phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl or quinolyl, wherein cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, $CF_3$, $OCF_3$, $OCH_2CF_3$, $OCHF_2$, $SCH_3$, $SOCH_3$, $SO_2CH_3$, $SCF_3$, phenyl or benzyl, wherein phenyl can be substituted by Cl.

Particular preference is given to compounds of formula I, in which A is described by:

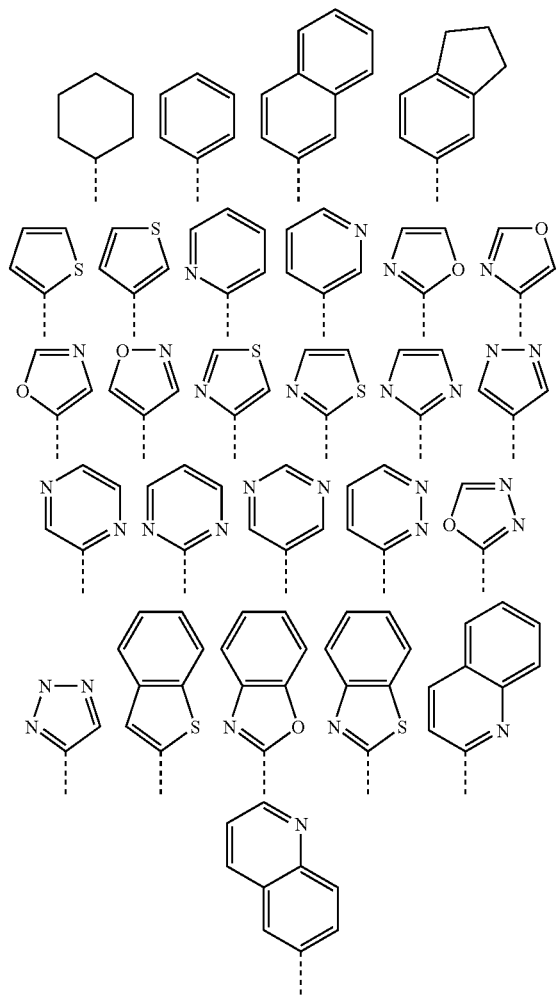

wherein cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, $CF_3$, $OCF_3$, $OCH_2CF_3$, $OCHF_2$, $SCH_3$, $SOCH_3$, $SO_2CH_3$, $SCF_3$, phenyl and benzyl, wherein phenyl can be substituted by Cl.

Also particular preference is given to compounds, wherein A is described as cyclohexyl or an aryl or heteroaryl radical selected from phenyl, naphthyl, indanyl, thienyl, pyridyl, thiazolyl, pyrazinyl, pyrimidinyl, pyridazinyl, benzothiophenyl, benzothiazolyl or quinolyl, wherein cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl.

More particular preference is given to compounds of formula I, in which A is described by phenyl, pyridyl or benzothiazolyl; which are unsubstituted or substituted by 1, 2 or 3 radicals selected from the group consisting of F, Cl, Br, alkyl having 1, 2, 3 or 4 carbon atoms, $CF_3$, $OCF_3$ and $SCF_3$.

Most particular preference is given to compounds, in which A is described by phenyl, pyridyl or benzothiazolyl, which are unsubstituted or substituted by $CF_3$, $OCF_3$ or $SCF_3$; preferably phenyl is substituted by $CF_3$, $OCF_3$ or $SCF_3$, pyridyl is substituted by $CF_3$ and benzothiazolyl is unsubstituted.

In another embodiment A in compounds of formula I is described by unsubstituted cycloalkyl having 3, 4, 5, 6, 7 or 8 carbon atoms, heterocycle, aryl or heteroaryl, in which the cycloalkyl or heterocycle radical can be condensed to an aryl radical and in which the aryl or heteroaryl radical can be condensed to an cycloalkyl or heterocycle radical.

In another embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is substituted by 1, 2 or 3 radicals and wherein the aryl or heteroaryl radical can be condensed to an cycloalkyl or heterocycle radical and wherein the aryl or heteroaryl radical is unsubstituted or substituted by 1, 2, 3 or 4 radicals; preference is given to compounds of the formula I in which A is described by a monocyclic ring compound, for example a monocyclic cycloalkyl having 3, 4, 5, 6, 7 or 8 carbon atoms, heterocycle, aryl or heteroaryl, which is at least substituted once in a position not near to the binding site of the cycloalkyl, heterocycle, aryl or heteroaryl to the linker B, for example phenyl or cyclohexyl radicals are at least substituted in position 4 and are optionally additionally substituted by additional radicals; preference is further given to compounds of the formula I in which A is described by a bicyclic ring compound, for example a bicyclic aryl, a bicyclic heteroaryl, a cycloalkyl or heterocycle radical to which an aryl or heteroaryl radical is condensed or an aryl or heteroaryl radical to which an cycloalkyl or heterocycle is condensed, where this bicyclic ring compound is unsubstituted or substituted with small substituents, in particular with F, Cl, $CF_3$, CN or methoxy, preferably in a position not near the binding site of the cycloalkyl, heterocycle, aryl or heteroaryl to the linker B, for example in 2-benzthiazolyl radicals in position 6 and/or 7 and in 2-naphthalene radicals in position 6.

In a further embodiment B in compounds of formula I is described as —O—C(R11R12)-, —C≡C—, —C(R13R14)-C(R15R16)-, —NR17-C(R18R19)- or —NR20-C(O)—, wherein R11, R12, R13, R14, R15, R16, R17, R18, R19 and R20 are, independently of one another, hydrogen or alkyl having 1, 2, 3 or 4 carbon atoms; preference is given to compounds, wherein B is —O—(CR11R12)-, —C≡C— or —CR13R14CR15R16-, wherein R11, R12, R13, R14, R15 and R16 are, independently of one another, hydrogen or alkyl having 1, 2, 3 or 4 carbon atoms, preferably when R11, R13, R14, R15 and R16 are hydrogen and R12 is hydrogen or alkyl having 1, 2, 3 or 4 carbon atoms, for example methyl; more preference is given to compounds, wherein B is —O—(CR11R12)-, preferably when R11 is hydrogen and R12 is hydrogen or alkyl having 1, 2, 3 or 4 carbon atoms, for example methyl.

Linker B is attached with its left hand side to the ring system and with its right hand side to the residue A.

In a further embodiment of compounds of formula I
R1 is hydrogen or alkyl having 1, 2, 3, 4, 5 or 6 carbon atoms
  which can be unsubstituted or substituted by 1, 2, 3, 4 or 5
  radicals selected from the group consisting of F, Cl, Br,
  I, $—O_i—(CH_2)_j—R25$;
  i is 0 or 1;
  j is 0, 1, 2 or 3;
  R25 is hydrogen or phenyl, heteroaryl having 5 or 6 atoms,
  cycloalkyl having 3, 4, 5 or 6 carbon atoms or heterocyclyl having 3, 4 5, 6, 7 or 8 atoms;
preferably, R1 is not hydrogen;
and
R2 is alkyl having 1, 2, 3, 4, 5 or 6 carbon atoms or phenyl,
  wherein alkyl is unsubstituted or substituted by 1, 2, 3, 4 or
  5 radicals selected from the group consisting of F, Cl, Br,
  I, $—O_m—(CH_2)_n—R26$;
  m is 0, or 1;
  n is 0, 1, 2 or 3;
  R26 is hydrogen, phenyl, heteroaryl having 5 or 6 atoms,
  cycloalkyl having 3, 4, 5 or 6 carbon atoms or heterocyclyl having 3, 4 5, 6, 7 or 8 atoms, in which the phenyl,
  heteroaryl, cycloalkyl or heterocyclyl are unsubstituted
  or substituted by 1, 2, or 3 radicals selected from F, Cl, Br
  or I;
  and wherein phenyl is unsubstituted or substituted by 1, 2,
  3, 4 or 5 radicals selected from the group consisting of F,
  Cl, Br, I, OH, CN, $NO_2$, $SCF_3$, $SF_5$, alkyl having 1, 2, 3,
  4, 5 or 6 carbon atoms, in which 1, 2, 3, 4, 5, 6, 7, 8, 9, 10,
  11, 12 or 13 hydrogen atoms may be substituted by
  fluorine atoms;
or, in another embodiment,
R1 and R2
  form, together with the carbon atom to which they are
  attached, a 3-, 4-, 5- or 6-membered saturated or partly
  saturated carbon ring, which can be condensed to phenyl; preferably, the formed ring is not condensed;
    wherein the formed ring and the optionally condensed
    phenyl can be unsubstituted or substituted by 1, 2, 3,
    4 or 5 radicals selected from the group consisting of F,
    Cl, Br, I, CN, $NO_2$, $SCF_3$, $SF_5$, or alkyl having 1, 2, 3
    or 4 carbon atoms;
or, in another embodiment,
R1 and R2
  form, together with the carbon atom to which they are
  attached, a 4-, 5- or 6-membered saturated or partly
  saturated carbon ring, wherein one carbon atom, which
  is not adjacent to the carbon atom to which R1 and R2
  are attached, is replaced by —O—, —NR58- or
  $—S(O)_w—$, and in which the formed ring can optionally
  be condensed to phenyl; preferably the formed ring is
  not condensed;
    wherein the formed ring and the optionally condensed
    phenyl can be unsubstituted or substituted by 1, 2, 3,
    4 or 5 radicals selected from the group consisting of F,
    Cl, Br, I, CN, $NO_2$, $SCF_3$, $SF_5$, or alkyl having 1, 2, 3
    or 4 carbon atoms;
    R58 is hydrogen, alkyl having 1, 2, 3 or 4 carbon
    atoms or C(O)R58;
      R59 is hydrogen, alkyl with 1, 2, 3 or 4 carbon
      atoms or phenyl;
    preferably, R58 is hydrogen or alkyl having 1, 2, 3 or
    4 carbon atoms;
  w is 0, 1 or 2;
  preferably w is 0.

In a preferred embodiment of compounds of formula I
R1 is hydrogen or alkyl having 1, 2, 3, 4, 5 or 6 carbon atoms;
  preferably, R1 is alkyl having 1, 2, 3, 4, 5 or 6 carbon atoms;
  and
R2 is alkyl having 1, 2, 3, 4, 5 or 6 carbon atoms or phenyl;
  wherein alkyl is unsubstituted or substituted by 1, 2, 3, 4 or
  5 radicals selected from the group consisting of F, Cl, Br,
  I, $—O_m—(CH_2)_n—R26$;
  m is 0, or 1;
  n is 0, 1, 2 or 3;
  R26 is hydrogen, phenyl, heteroaryl having 5 or 6 atoms,
  cycloalkyl having 3, 4, 5 or 6 carbon atoms or heterocyclyl having 3, 4 5, 6, 7 or 8 atoms, in which the phenyl,
  heteroaryl, cycloalkyl or heterocyclyl are unsubstituted
  or substituted by 1, 2, or 3 radicals selected from F, Cl, Br
  or I;
  preferably, R26 is hydrogen or phenyl;
or, in another preferred embodiment,
R1 and R2
  form, together with the carbon atom to which they are
  attached, a 3-, 4, 5- or 6-membered saturated or partly
  saturated carbon ring, which can be condensed to phenyl; preferably the ring is not condensed;
or, in another preferred embodiment,
R1 and R2
  form, together with the carbon atom to which they are
  attached, a 4-, 5- or 6-membered saturated or partly
  saturated carbon ring, wherein one carbon atom, which
  is not adjacent to the carbon atom to which R1 and R2
  are attached, is replaced by —O—, —NH— or —S—;
  preferably the ring is saturated, and preferably one carbon atom, which is not adjacent to the carbon atom to
  which R1 and R2 are attached, is replaced by —O— or
  —S—.
In a more preferred embodiment
R1 is alkyl having 1, 2, 3 or 4 carbon atoms;
and
R2 is alkyl having 1, 2, 3 or 4 carbon atoms, phenyl or benzyl;
or, in another more preferred embodiment,
R1 and R2
  form, together with the carbon atom to which they are
  attached, a cyclopropane, cyclobutane, cyclopentane,
  cyclohexane, cyclopentene ring or indene;
  preferably R1 and R2 form a cyclopropane, cyclobutane,
  cyclopentane, cyclohexane or cyclopentene ring;
or, in another more preferred embodiment,
R1 and R2
  form, together with the carbon atom to which they are
  attached, a tetrahydro-thiophene or tetrahydro-thiopyrane ring.
In a most preferred embodiment
R1 is methyl or ethyl; more preferably, methyl;
and
R2 is methyl or ethyl
or, in another most preferred embodiment,
R1 and R2
  form, together with the carbon atom to which they are
  attached, a cyclobutane or cyclopentane ring.
  In given embodiments of the present invention one or more
or all of the groups contained in the compounds of formula I
can independently of each other have any of the given, preferred, more preferred or most preferred definitions of the
groups specified above or any one or some of the specific
denotations which are comprised by the definitions of the
groups and specified above, all combinations of given or
preferred definitions, more preferred or most preferred and/or
specific denotations being a subject of the present invention.

Special preference is given to the following compounds of the formula I, selected from the group consisting of:
2-Methyl-2-{[1-(4-trifluoromethoxy-benzyloxy)-5,6,7,8-tetrahydro-naphthalene-2-carbonyl]-amino}-propionic acid;
2-{[1-(Benzothiazol-2-ylmethoxy)-5,6,7,8-tetrahydro-naphthalene-2-carbonyl]-amino}-2-methyl-propionic acid;
2-Methyl-2-{[1-(4-trifluoromethyl-benzyloxy)-5,6,7,8-tetrahydro-naphthalene-2-carbonyl]-amino}-propionic acid;
2-Methyl-2-{[1-(6-trifluoromethyl-pyridin-3-ylmethoxy)-5,6,7,8-tetrahydro-naphthalene-2-carbonyl]-amino}-propionic acid;
2-{[1-(Benzothiazol-2-ylmethoxy)-5,6,7,8-tetrahydro-naphthalene-2-carbonyl]-amino}-2-methyl-butyric acid;
2-Methyl-2-{[1-(4-trifluoromethyl-benzyloxy)-5,6,7,8-tetrahydro-naphthalene-2-carbonyl]-amino}-butyric acid;
2-Methyl-2-{[1-(6-trifluoromethyl-pyridin-3-ylmethoxy)-5,6,7,8-tetrahydro-naphthalene-2-carbonyl]-amino}-butyric acid;
2-{[1-(2-Fluoro-4-trifluoromethyl-benzyloxy)-5,6,7,8-tetrahydro-naphthalene-2-carbonyl]-amino}-2-methyl-propionic acid;
2-Methyl-2-{[1-(4-trifluoromethoxy-benzyloxy)-5,6,7,8-tetrahydro-naphthalene-2-carbonyl]-amino}-butyric acid;
2-{[1-(2-Fluoro-4-trifluoromethyl-benzyloxy)-5,6,7,8-tetrahydro-naphthalene-2-carbonyl]-amino}-2-methyl-butyric acid;
2-Methyl-2-{[7-methyl-4-(4-trifluoromethyl-benzyloxy)-indane-5-carbonyl]-amino}-propionic acid;
2-Methyl-2-{[7-(4-trifluoromethyl-benzyloxy)-benzo[b]thiophene-6-carbonyl]-amino}-propionic acid;
2-Methyl-2-{[4-(4-trifluoromethyl-benzyloxy)-benzo[b]thiophene-5-carbonyl]-amino}-propionic acid; or
2-Methyl-2-{[4-(5-trifluoromethyl-pyridin-2-ylmethoxy)-benzo[b]thiophene-5-carbonyl]-amino}-propionic acid
and/or a pharmaceutically acceptable salt and/or a prodrug thereof.

The compounds of the formula I can be present in the form of their salts. An overview of pharmaceutically employed salts can be found in the "Handbook of Pharmaceutical Salts", edited by P. Heinrich Stahl, Camille G. Wermuth, Verlag Helvetica Chimica Acta, Switzerland, 2002. Suitable base addition salts are salts of all pharmacologically acceptable bases, for example alkali metal, earth alkali metal or metal salts, preferably sodium, potassium, magnesium, calcium or zink salts, or as ammonium salts, for example as salts with ammonia or organic amines or amino acids, preferably as salts formed with ammonia, arginine, benethamine, benzathine, choline, deanol, diethanolamine, diethylamine, 2-(diethylamino)-ethanol, ethanolamine, ethylendiamine, N-methyl-glucamine, hydrabamine, 1H-imidazole, lysine, 4-(2-hydroxyethyl)-morpholine, piperazine, 1-(2-hydroxyethyl)-pyrrolidine, triethanolamine or tromethamine; If the compounds contain a basic group, they are capable of forming salts with acid, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerolphosphates, maleates, benzoates, oxalates and pamoates. This group also corresponds to the physiologically acceptable anions; but also trifluoroacetates. They can also be present as zwitterions.

If the inventive compounds contain one or more centers of asymmetry, these may independently of one another have the S and the R configuration. The compounds may be in the form of optical isomers, of diastereomers, of racemates or of mixtures thereof in any ratio.

The compounds of the formula I according to the invention can contain mobile hydrogen atoms, that is be present in various tautomeric forms. The present invention relates to all the tautomers of the compounds of the formula I.

The present invention furthermore encompasses derivatives of compounds of the formula I, for example solvates, such as hydrates and adducts with alcohols, esters, prodrugs and other physiologically tolerated derivatives of compounds of the formula I, and also active metabolites of compounds of the formula I. Further the invention contains all crystal modifications of compounds of formula I.

The invention relates, in particular, to prodrugs of the compounds of the formula I which are not necessarily pharmacologically active in vitro but which are converted in vivo, under physiological conditions, into active compounds of the formula I, for example by hydrolysis in blood. The skilled person is familiar with suitable prodrugs for the compounds of the formula I, that is chemically modified derivatives of the compounds of the formula I possessing properties which have been improved in a desired manner. Further details with regard to prodrugs can be found, for example, in Fleisher et al., Advanced Drug Delivery Reviews 19 (1996) 115-130; Design of Prodrugs, H. Bundgaard, Ed., Elsevier, 1985; or H. Bundgaard, Drugs of the Future 16 (1991) 443. Prodrugs which are especially suitable for the compounds of the formula I are ester prodrugs of carboxylic acid groups, amide prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom which is located on a nitrogen atom is replaced with an acyl group or carbamate group. Examples of ester prodrugs and amide prodrugs which may be prepared from the carboxylic acid group in a compound of formula I and which may be mentioned are $(C_1$—$C_4)$-alkyl esters such as methyl esters, ethyl esters, n-propyl esters, isopropyl esters, n-butyl esters and isobutyl esters, substituted alkyl esters such as hydroxyalkyl esters, acyloxyalkyl esters, aminoalkyl esters, acylaminoalkyl esters and dialkylaminoalkyl esters, unsubstituted amides and N—$(C_1$—$C_4)$-alkylamides, such as methylamides or ethylamides. For example the methyl and ethyl esters of the compounds listed above are included.

Alkyl radicals may be straight-chain or branched. This also applies if they carry substituents or occur as substituents of other radicals, for example in alkylamino, alkoxy, arylalkyl, heteroarylalkyl, fluoroalkyl or —$SO_f$-alkyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. Where indicated, one or more, for example 1, 2, 3, 4, 5, 6, 7, 8, 9, 10, 11, 12 or 13, hydrogen atoms in alkyl radicals may be replaced by fluorine atoms to form fluoroalkyl radicals. Examples of such radicals are difluoromethyl, trifluoromethyl, pentafluoroethyl, 2,2,2-trifluoroethyl; 3,3,3-trifluoropropyl; 3,3,3-trifluorobutyl, 4,4,4-trifluorbutyl.

Examples of cycloalkyl radicals are cyclopropyl, cyclobutyl, cyclopentyl, cyclohexyl, cycloheptyl or cyclooctyl, in particular cyclopentyl or cylcohexyl. Cycloalkyl radicals can be saturated or partly unsaturated, especially when they are condensed to an aryl or heteroaryl radical. For example a cycloalkyl radical may contain zero, one or two double bonds. This also applies if they carry substituents or occur as substituents of other radicals, for example in the radical cycloalkylalkyl. One or more, for example 1, 2, 3, 4, 5, 6, 7, 8, 9, 10, 11, 12 or 13, hydrogen atoms in cycloalkyl radicals may be replaced by fluorine atoms to form fluorocycloalkyl radicals. Substituted cycloalkyl radicals may be substituted in identical or different positions. Where for a cycloalkylalkyl or cycloalkylalkoxy radical the number of carbon atoms has been given, this is the sum of the number of the carbon atoms in the cycloalkyl and in the alkyl or alkoxy radical, respectively.

Heterocycle radicals are, if not indicated otherwise, monocyclic or bicyclic saturated or partly unsaturated 5, 6, 7, 8, 9 or 10-membered ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms, in particular two oxygen atoms. Heterocycle radicals includes heterocycloalkyls and heterocycloalkenyls and, therefore, they can be saturated or partly unsaturated. Where indicated, a heterocycle may be condensed to an aryl or heteroaryl radical, for example to form 2,3-Dihydro-benzo[1,4]dioxine. For example a heterocycle radical may contain zero, one or two double bonds. The heterocycle radicals may be attached by all positions, for example by the 1 position, 2 position, 3 position, 4 position, 5 position, 6 position, 7 position or 8 position. Heterocycle radicals may be unsubstituted or be substituted one or more times, for example once, twice or three times, by identical or different radicals in identical or different positions. This applies likewise to heterocycle radicals such as, for example, in the radical heterocycloalkyl. Examples of heterocycles are oxirane, aziridine, tetrahydrofurane, tetrahydropyrane, dioxolane, for example 1,3-dioxolane, dioxane, for example 1,4-dioxan, piperidine, pyrrolidin, imidazolidine, triazolidine, hexahydropyrimidine, piperazine, tetrahydropyridazine, triazinane, for example, 1,3,5-triazinane, 1,2,3-triazinane or 1,2,4-triazinane, tetrahydrothiophene, tetrahydrothiopyrane, dithiolane, for example 1,3-dithiolane, dithiane, thiazolidine, oxazolidine, oxathiolane, for example 1,3-oxathiolane, morpholine or thiomorpholine, in particular piperidine, 1,3-dioxolane and 1,4-dioxane.

The aryl radicals are chosen from phenyl, 1-naphthyl, 2-naphthyl and indenyl. Aryl radicals may be unsubstituted or be substituted one or more times, for example once, twice or three times, by identical or different radicals. If a aryl radical is substituted, it preferably has one, two or three identical or different substituents. This likewise applies to substituted aryl radicals in groups such as, for example, arylalkyl or aryloxy. Where indicated, aryl radicals may be condensed to a cycloalkyl or heterocycle radical, for example to form 2,3-Dihydro-benzo[1,4]dioxine, Benzo[1,3]dioxole or indane.

Heteroaryl radicals are monocyclic or bicyclic aromatic 5, 6, 7, 8, 9 or 10-membered ring compounds or, where indicated, 5 or 6 membered ring compounds, in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or substituted one or more times, for example once, twice or three times, by identical or different radicals. This applies likewise to heteroaryl radicals such as, for example, in the radical heteroarylalkyl. Where indicated, heteroaryl radicals may be condensed to a cycloalkyl or heterocycle radical. Examples of heteroaryl having 5 or 6 atoms are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl, tetrazolyl. Examples of other heteroaryls with more atoms are benzothiophenyl, benzofuranyl, indolyl, isoindolyl, indazolyl, quinolyl, isoquinolyl, benzimidazolyl, benzothiazolyl, benzoxazolyl, benzotriazolyl, benzoxadiazolyl, benzothiadiazolyl, quinoxalinyl, quinazolinyl, cinnolinyl, phthalazinyl, quinolizinyl, purinyl, pteridinyl and thienothiazolyl. Also encompassed are the corresponding N-oxides and S-dioxides of these compounds.

When any variable (e.g. aryl, R1) occurs more than one time in any constituent, its definition on each occurrence is independent of its definition at every other occurrence. Also, combinations of substituents and/or variables are permissible only if such combinations result in stable compounds.

The invention further relates to the following processes for preparing the compounds of the formula I.

The invention further relates to the following processes for preparing the compounds of the formula I.

Compounds of formula I can be prepared as described in Scheme 1

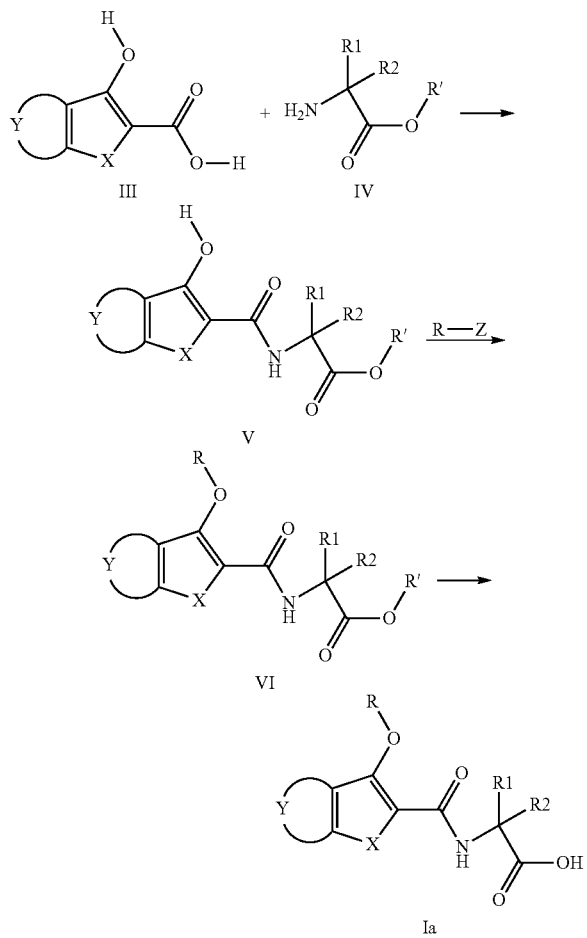

which comprises
a) coupling of an acid of formula III with an amino compound of formula IV to an amide of formula V,
b) reacting a compound of formula V with an reagent R-Z to an compound of formula VI,
c) converting an ester of formula VI to an acid of formula Ia wherein in the compounds of the formulae Ia, III, IV, V and VI X, Y, R1 and R2 are defined as in formula I, R is —C(R11R12)-A, wherein R11, R12 and A are defined as in formula I and B is —O—(CR11R12)-, Z is OH or L, wherein L is a leaving group, which can undergo nucleophilic substitution with an amine, and R' is alkyl having 1, 2, 3, 4, 5 or 6 carbon atoms.

The procedure for preparing the compounds of the formula I is initially a coupling of an amino compound of formula IV with an acid of formula III for preparing the compound of formula V generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 800, more preferably from 0° C. to 20° C. The reaction time is generally from 15 min to 6 days, preferably from 15 min to 16 h depending on the composition of the mixture and the chosen temperature range.

Subsequently, the transformation of the compound of formula V to the compound of formula VI can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively the reaction of the compound of formula V with R—OH (Z=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 800, more preferably from 0° C. to 25° C. The reaction time is generally from 15 min to 6 days, preferably from 15 min to 16 h, depending on the composition of the mixture and the chosen temperature range. The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Alternatively compounds of formula I can be prepared as described in Scheme 2

Scheme 2

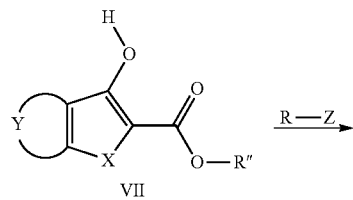

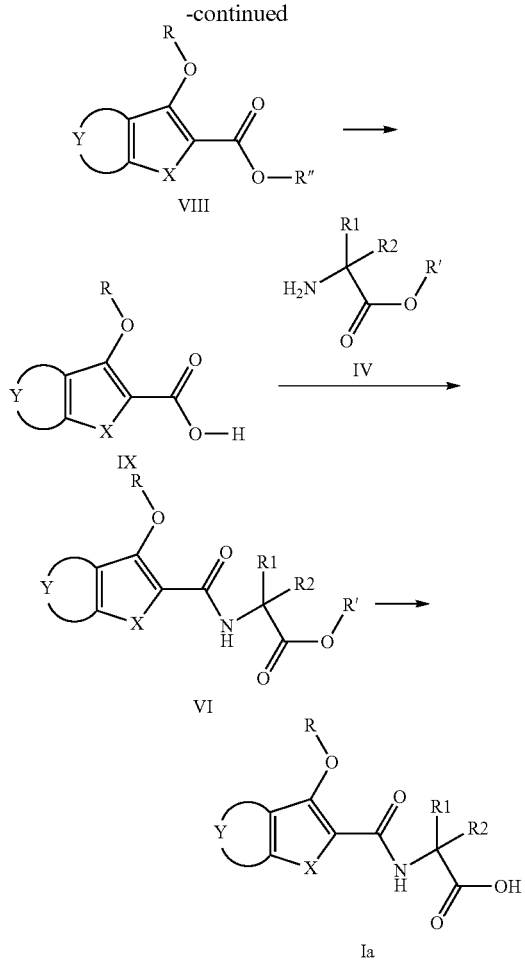

which comprises a) reacting a compound of formula VII with an reagent R-Z to a compound of formula VIII b) converting an ester of formula VIII to an acid of formula IX c) coupling of an acid of formula IX with an amino compound of formula IV to an amide of formula VI d) converting an ester of formula VI to an acid of formula Ia wherein in the compounds of the formulae Ia, IV, VI, VII, VIII and IX X, Y, R1 and R2 are defined as in formula I, R is —(CR11R12)-A, wherein R11, R12 and A are defined as in formula I and B is —O—(CR11R12)-, Z is OH or L, wherein L is a leaving group, which can undergo nucleophilic substitution with an amine, R' is alkyl having 1, 2, 3, 4, 5 or 6 carbon atoms, and R" is alkyl having 1, 2, 3, 4, 5 or 6 carbon atoms or aryl.

The procedure for preparing the compounds of the formula I is initially a transformation of the compound of formula VII to the compound of formula VIII which can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 1500. The reaction time is generally from 2 min to 6 days, preferably from 15 min to 16 h depending on the composition of the mixture and the chosen temperature range Alternatively the reaction of the compound of formula V with R—OH (Z=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 800, more preferably from 0° C. to 25° C. The reaction time is generally from 15 min to 6 days, preferably from 15 min to 16 h, depending on the composition of the mixture and the chosen temperature range. The subsequent cleavage of the ester of formula VIII to the acid of formula IX can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

The resulting compound of formula IX can be coupled with the amino compound of formula IV to form the compound of formula VI generally in the presence of an coupling agent, for example EDC, DIC or HATU and optionally an additional base, for example triethylamine or Hünig's base, in an appropriate solvent, in particular in an aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The optional cleavage of the ester of formula VI to the acid of formula Ia in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

Alternatively, compounds of formula I can be prepared as described in Scheme 3

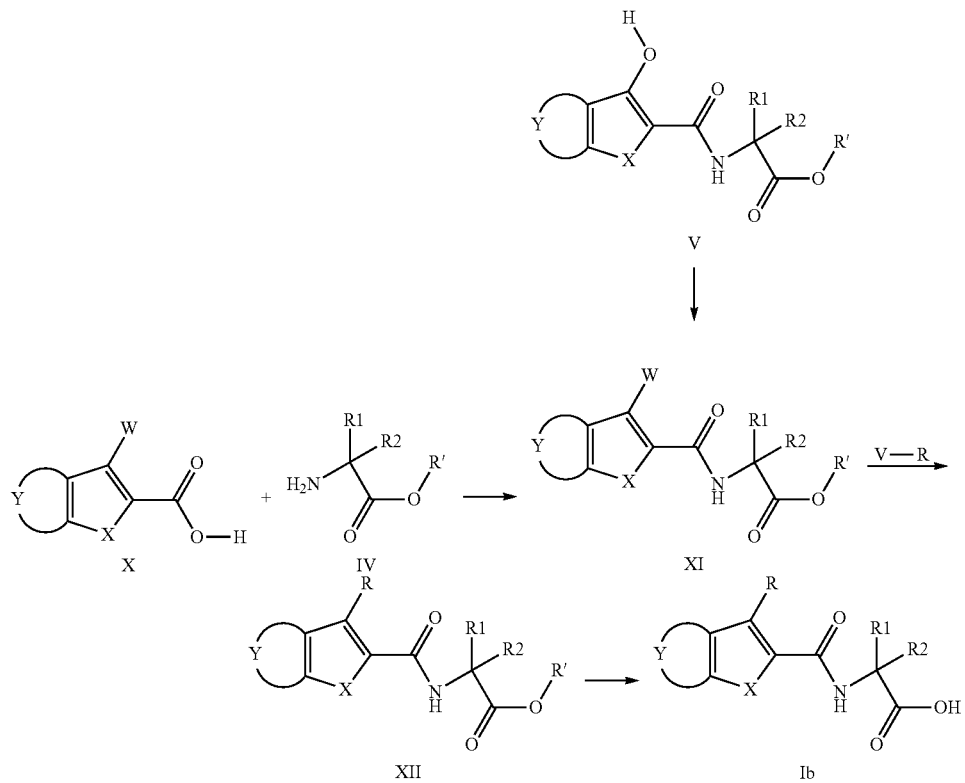

Scheme 3 which comprises
a) coupling of an acid of formula X with an amino compound of formula IV to an amide of formula XI,
or, alternatively, the conversion of a compound of formula V to a compound of formula XI (if W is triflate, mesylate or tosylate),
b) reacting a compound of formula XI with an reagent V—R to an compound of formula XII,
c) converting an ester of formula XII to an acid of formula Ib;
wherein in the compounds of the formulae Ib, IV, V, X, XI and XII
X, Y, R1 and R2 are defined as in formula I,
V—R is HC≡C-A and R is —C≡C-A,
or V—R is HCR52=CR53-A and R is —CR52=CR53-A,
or V—R is (R'''O)$_2$BCR52=CR53-A and R is —CR52=CR53-A,
or V—R is (R'''')$_3$SnCR52=CR53-A and R is —(R'''')$_3$SnCR52=CR53-A,
or V—R is HalZnCR52=CR53-A and R is —CR52=CR53-A, or V—R is HNR17-C(R18R19)-A and R is —NR17-C(R18R19)-A,
or V—R is HNR20-C(O)-A and R is —NR20-C(O)-A,
wherein R17, R18, R19, R20, R52, R53 and A are defined as in formula I,
W is halogen, for example I, Br or Cl, or triflate, mesylate or tosylate,
R' is alkyl having 1, 2, 3, 4, 5 or 6 carbon atoms,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
R'''' is alkyl having 1, 2, 3, 4, 5 or 6 carbon atoms,
Hal is halogen, for example I, Br or Cl.

The procedure for preparing the compounds of the formula I is initially a coupling of an amino compound of formula IV with an acid of formula X for preparing the compound of formula XI generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Alternatively, a compound of formula V can be converted into a compound of formula XI, in which W is defined as triflate, tosylate or mesylate, by reacting it with an anhydride or chloride of trifluoromethane sulfonic acid para-toluene sulfonic acid or methyl sulfonic acid in the presence of a suitable base, for example triethylamine in an appropriate solvent, for example dichloromethane. The reaction temperature in this case is generally from −80° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula XI to the compound of formula XII can be achieved by reacting with a reagent V—R, often under inert conditions and in an appropriate solvent, in the presence of a suitable catalytic system, which can contain a palladium and/or copper complex and/or salt, for example $Pd_2\,dba_3$, $Pd(Ph_3)_4$, $Pd(OAc)_2$ or CuI, optionally additional ligands as, for example, phosphine, amine or carbene ligands, and optionally auxiliaries like amines, pyridine, quaternary ammonium salts, CsF, $Ag_2CO_3$, $Na_2CO_3$, $K_2CO_3$, $Cs_2CO_3$, NaOtBu, KOtBu, NaOAc, KOAc, $K_3PO_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The cleavage of the ester of formula XII to the acid of formula Ib can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds of formulae Ib and XII in Scheme 3, in which R is defined as —C≡C-A can be (partially) hydrogenated to compounds of formulae Ib and XII, in which R is defined as —CH=CH-A or —CH$_2$CH$_2$-A, and compounds of formulae Ib and XII in Scheme 3, in which R is defined as —CR52=CR53-A can be hydrogenated to compounds of formulae Ib and XII, in which R is defined as —CHR52=CHR53-A. These transformations can be carried out in analogy to the processes which are described in the literature and are known to those skilled in the art, for example by (partial) hydrogenation of said compounds in the presence of homogenous or heterogenous catalysts.

Alternatively compounds of formula I can be prepared as described in Scheme 4

Scheme 4

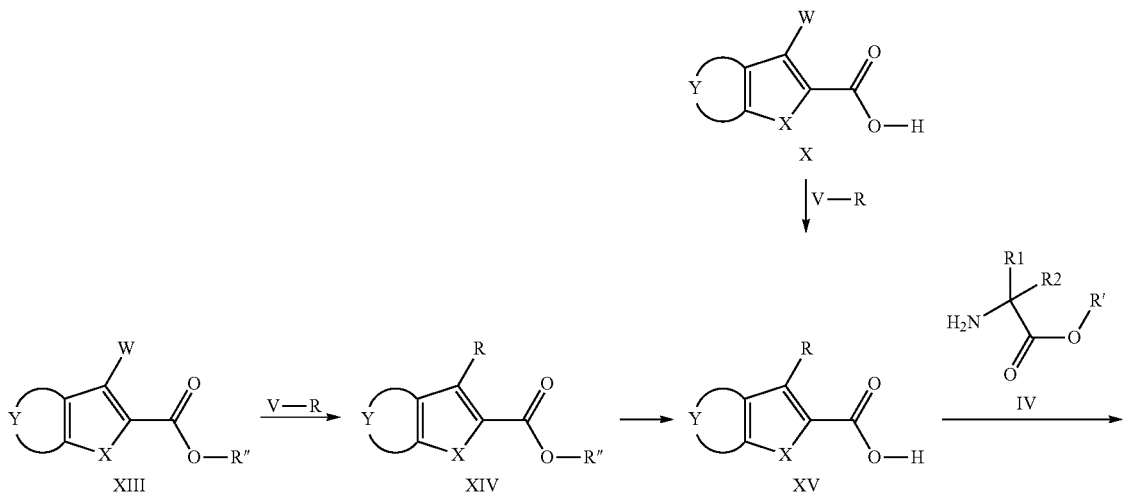

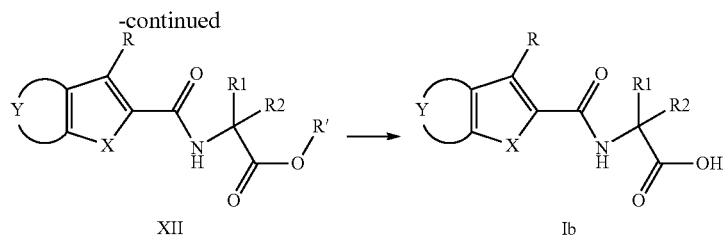

which comprises
a) reacting a compound of formula XIII with a reagent V—R to a compound of formula XIV
b) converting an ester of formula XIV to an acid of formula XV
or, alternatively, reacting a compound of formula X with a reagent V—R to a compound of formula XV
c) coupling of an acid of formula XV with an amino compound of formula IV to an amide of formula XII
d) converting an ester of formula XII to an acid of formula Ib
wherein in the compounds of the formulae Ib, IV, X, XII, XIII, XIV and XV
X, Y, R1 and R2 are defined as in formula I,
V—R is HC≡C-A and R is —C≡C-A,
or V—R is HCR52=CR53-A and R is —CR52=CR53-A,
or V—R is (R'''O)$_2$BCR52=CR53-A and R is —CR52=CR53-A,
or V—R is (R'''')$_3$SnCR52=CR53-A and R is —(R'''')$_3$SnCR52=CR53-A,
or V—R is HalZnCR52=CR53-A and R is —CR52=CR53-A,
or V—R is HNR17-C(R18R19)-A and R is —NR17-C(R18R19)-A,
or V—R is HNR20-C(O)-A and R is —NR20-C(O)-A,
wherein R17, R18, R19, R20, R52, R53 and A are defined as in formula I,
W is halogen, for example I, Br or Cl, or triflate, mesylate or tosylate,
R' is alkyl having 1, 2, 3, 4, 5 or 6 carbon atoms,
R'' is alkyl having 1, 2, 3, 4, 5 or 6 carbon atoms or aryl,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
R'''' is alkyl having 1, 2, 3, 4, 5 or 6 carbon atoms,
Hal is halogen, for example I, Br or Cl.

The procedure for preparing the compounds of the formula I is initially a transformation of the compound of formula XIII to the compound of formula XIV which can be achieved by reacting with a reagent V—R, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAC, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The subsequent cleavage of the ester of formula XIV to the acid of formula XV can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

Alternatively, a transformation of a compound of formula X to the compound of formula XV can be achieved by reacting with a reagent V—R, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The resulting compound of formula XV can be coupled with the amino compound of formula IV to form the compound of formula XII generally in the presence of a coupling agent, for example EDC, DIC or HATU and optionally an additional base, for example triethylamine or Hünig's base, in an appropriate solvent, in particular in aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The cleavage of the ester of formula XII to the acid of formula Ib in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range. The optional derivatisation of the compounds of the formulae XII or Ib to compounds of formula I, in which D is not defined as C(O)OH, can be carried out in analogy to the processes which are described in the literature and are known to those skilled in the art, for example by reaction of compounds of formula Ia with oxalyl chloride followed by the reaction with a sulfonamide in the presence of a suitable base like sodium hydride.

Optionally, compounds of formulae XIV, XV, XII and Ib in Scheme 4, in which R is defined as —C≡C-A can be (partially) hydrogenated to compounds of formulae XIV, XV, XII and Ib, in which R is defined as —CH=CH-A or —CH₂CH₂-A, and compounds of formulae XIV, XV, XII and Ib in Scheme 4, in which R is defined as —CR52=CR53-A can be hydrogenated to compounds of formulae XIV, XV, XII and Ib, in which R is defined as —CHR52=CHR53-A. These transformations can be carried out in analogy to the processes which are described in the literature and are known to those skilled in the art, for example by (partial) hydrogenation of said compounds in the presence of homogenous or heterogenous catalysts.

Compounds of formula I can be prepared as described in Scheme 5

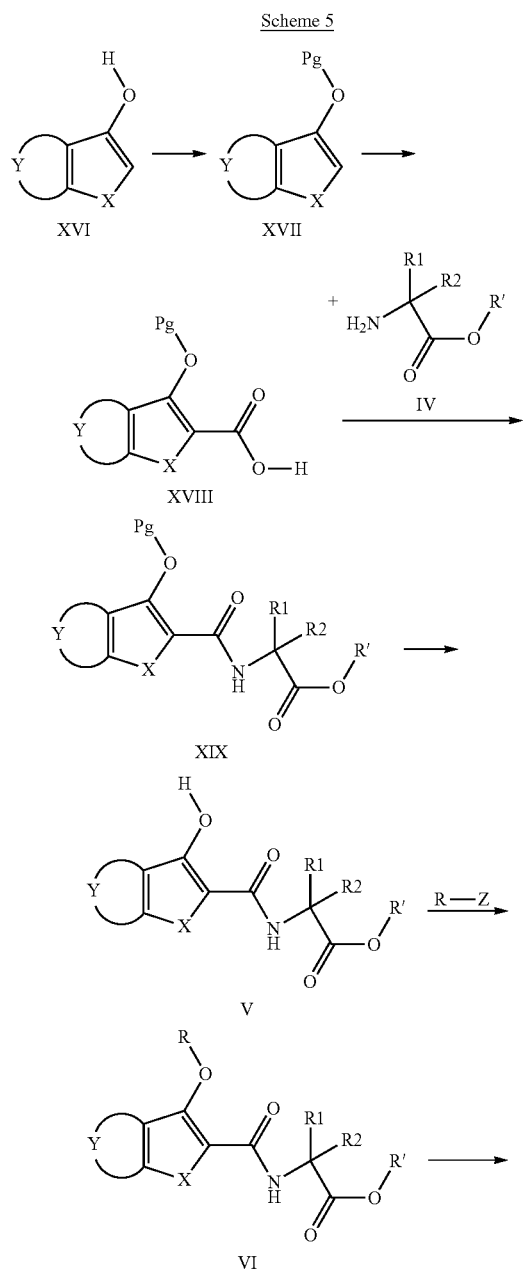

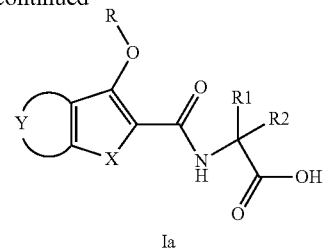

which comprises
a) protecting the hydroxy group in a compound of formula XVI to obtain a compound of formula XVII,
b) introducing a carboxy group in ortho-position to the protected hydroxy group in a compound XVII to obtain an acid of formula XVIII
c) coupling of an acid of formula XVIII with an amino compound of formula IV to an amide of formula XIX,
d) deprotecting the hydroxy group in a compound of formula XIX to obtain a compound of formula V
e) reacting a compound of formula V with a reagent R-Z to a compound of formula VI,
f) converting an ester of formula VI to an acid of formula Ia
wherein in the compounds of the formulae Ia, IV, V, VI, XVI, XVII, XVII and XIX
X, Y, R1 and R2 are defined as in formula I,
R is —C(R11R12)-A, wherein R11, R12 and A are defined as in formula I and
B is —O—(CR11R12)-,
Z is OH or L, wherein L is a leaving group, which can undergo nucleophilic substitution with an amine,
R' is alkyl having 1, 2, 3, 4, 5 or 6 carbon atoms, and
Pg is a protecting group for (aromatic) hydroxy functions, which has an ortho-directing effect in a metalation reaction, for example a lithiation, and which can be cleaved in the presence of a primary or secondary alkyl ester and an amide, for example Pg is a methoxymethyl group.

The procedure for preparing the compounds of the formula I is initially a protection of a hydroxy group of the compound of formula XVI with a protecting group Pg, which has an ortho-directing effect in a metalation reaction, for example a lithiation, and which can be cleaved in the presence of a primary or secondary alkyl ester and an amide, for example Pg is a methoxymethyl group. The protection of a compound of formula XVI to the compound of formula XVII can be achieved by adding, for example methoxymethylchloride or -bromide in the presence of a suitable base, for example sodium hydride in a suitable solvent, for example DMF or THF. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Subsequently, the transformation of the compound of formula XVII to the compound of formula XVIII can be achieved by a metalation ortho to the hydroxy group protected with an ortho-directing protecting group and a carboxylation; this can be achieved by reacting the compound of formula XVII in a suitable solvent, for example diethyl ether or THF, with a metallation reagent, for example a lithiation reagent as n-butyl-lithium, sec-butyl-lithium or tert-butyl-lithium, optionally in the presence of a chelating agent, such as, for example, N,N,N',N'-tetramethylethylenediamine (TMEDA) and by treating the reaction subsequently with, for example, with carbon dioxide. The reaction temperature in this case is generally from −100° C. to 150° C., preferably from −80° C. to 100°, more preferably from −80° C. to 20° C. The reaction time is generally from 15 min to 6 days, preferably from 15 min to 16 h depending on the composition of the mixture and the chosen temperature range. The next transformation is a coupling of an amino compound of formula IV with an acid of formula XVIII for preparing the compound of formula XIX generally in the presence of an coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range. The subsequent transformation is a cleavage of the ortho directing protecting group Pg of the compound of formula XIX to obtain the compound or formula V. This can be achieved, for example in the case, where Pg is a methoxymethyl group by reacting the compound of formula XIX in the presence of an acid, for example hydrochloric acid, in a suitable solvent as for example, THF and isopropanol. The reaction temperature in this case is generally from 0° C. to 200° C., preferably from 20° C. to 80° C. The reaction time is generally from 2 min to 6 days, preferably from 2 min to 16 h, depending on the composition of the mixture and the chosen temperature range. Subsequently, the transformation of the compound of formula V to the compound of formula VI can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively, the reaction of the compound of formula V with R—OH (Z=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range. The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

The compounds of formula Ia and Ib are contained in the compound of formula I.

The starting compounds of the formulae III, IV, V, VII, X, XIII and XVI are commercially available or can be prepared by a skilled artisan according to procedures described in the literature.

The workup and optionally the purification of the products and/or intermediates are effected by the customary methods such as extraction, chromatography or crystallization and the customary dryings.

Alternative processes for preparing the compounds are described in the examples and are also part of the invention.

Functional groups in the starting compounds may be present in protected form or in the form of precursors, and then be converted into the desired groups in the compounds of the formula I prepared by the process described above. Corresponding protective group techniques are known to the skilled artisan.

It is likewise possible for appropriate functional groups to be derivatized by methods known to the skilled artisan.

Another aspect of the invention is the use of a compound of the formula I and/or a pharmaceutically acceptable salt and/or a prodrug thereof alone or in combination with other medicaments or active ingredients as for producing a medicament for the treatment or prophylaxis of chemokine mediated diseases.

The invention further relates to the use of a compound of the formula I and/or a pharmaceutically acceptable salt and/or a prodrug thereof alone or in combination with other medicaments or active ingredients as for producing a medicament for the treatment or prophylaxis of a chemokine mediated disease, wherein the chemokine binds to a CXC receptor.

Another aspect of the invention is the use of a compound of the formula I and/or the pharmaceutically acceptable salt and/or a prodrug thereof alone or in combination with other medicaments or active ingredients as for producing a medicament for the treatment or prophylaxis of a chemokine mediated disease, wherein the chemokine binds to a CXCR2 and/or CXCR1 receptor, in particular to a CXCR2 receptor.

The invention further relates to the use of a compound of the formula I and/or a pharmaceutically acceptable salt and/or a prodrug thereof alone or in combination with other medicaments or active ingredients as for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer. In particular, a compound of formula I is used alone.

As a further aspect of the present invention, certain compounds of formula I may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

Also claimed is a medicine or pharmaceutical composition for human or veterinary use, comprising an effective amount of a compound of the formula I and/or a pharmaceutically acceptable salt and/or a prodrug thereof, together with pharmaceutically acceptable carriers and additives, alone or in combination with other active pharmaceutical ingredients or medicaments.

Medicaments which comprise a compound of the formula I and/or a pharmaceutically acceptable salt and/or a prodrug thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or a pharmaceutically acceptable salt and/or a prodrug thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or a pharmaceutically acceptable salt and/or a prodrug thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or a pharmaceutically acceptable salt and/or a prodrug thereof for a patient weighing about 75 kg is at least 0.001 mg/kg, preferably 0.01 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

| List of abbreviations: | |
|---|---|
| O-(7-Azabenzotriazol-1-yl)-N,N,N',N'-tetramethyluronium Hexafluorophosphate | HATU |
| [2-(1H)-benzotriazol-1yl]-1,1,3,3-tetramethyluronium tetra-fluoroborate | TBTU |
| N-Brom-succinimide | NBS |
| Dichloromethane | DCM |
| 4-Dimethylaminopyridine | DMAP |
| Diethylazodicarboxylate | DEAD |
| Diisoppropylazodicarboxylate | DIAD |
| N,N'-Diisopropylcarbodiimid | DIC |
| 1-(3-Dimethylaminopropyl)-3-ethylcarbodiimide-Hydrochloride | EDC |
| N,N-Dimethylformamide | DMF |
| Electron spray ionisation Positive mode | ESI+ or ESI |
| Electron spray ionisation Negative mode | ESI− |
| Tetrahydrofuran | THF |
| N,N,N',N'-Tetramethylethylendiamine | TMEDA |
| Retention time | Rt |

The following examples are part of and intended to illustrate but not limit the present invention.

EXAMPLE 1

2-Methyl-2-{[1-(4-trifluoromethoxy-benzyloxy)-5,6,7,8-tetrahydro-naphthalene-2-carbonyl]-amino}-propionic acid

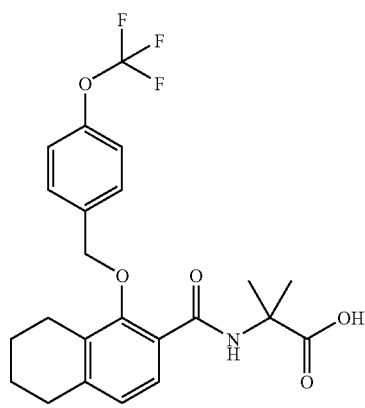 [SMILES: CC(C)(NC(=O)c1ccc2c(c1OCc1ccc(OC(F)(F)F)cc1)CCCC2)C(=O)O]

a) 2-Methyl-2-{[1-(4-trifluoromethoxy-benzyloxy)-5,6,7,8-tetrahydro-naphthalene-2-carbonyl]-amino}-propionic acid methyl ester 0.16 g 2-[(1-hydroxy-5,6,7,8-tetrahydro-naphthalene-2-carbonyl)-amino]-2-methyl-propionic acid methyl ester, 0.36 g cesium carbonate, 0.21 g of 1-bromomethyl-4-trifluoromethoxy-benzene and 18.3 mg potassium iodide were dissolved in 20 ml of N,N-di-methylformamide and stirred overnight at room temperature. 10 ml of diethyl ether and 10 ml of water were added to the reaction. The organic layer was separated and washed again with 10 ml of water. It was then dried over magnesium sulphate, filtered and concentrated in vacuo. Purification by flash chromatography (silica, heptanes/ethyl acetate) afforded 168 mg of 2-methyl-2-{[1-(4-trifluoromethoxy-benzyloxy)-5,6,7,8-tetrahydro-naphthalene-2-carbonyl]-amino}-propionic acid methyl ester.

$C_{24}H_{26}F_3NO_5$ (465.18), LCMS (ESI): 466.18 (MH$^+$).

b) 2-Methyl-2-{[1-(4-trifluoromethoxy-benzyloxy)-5,6,7,8-tetrahydro-naphthalene-2-carbonyl]-amino}-propionic acid 0.13 g 2-methyl-2-{[1-(4-trifluoromethoxy-benzyloxy)-5,6,7,8-tetrahydro-naphthalene-2-carbonyl]-amino}-propionic acid methyl ester was dissolved in 5 ml of tetrahydrofuran and 0.5 ml of methanol. To this was added 0.42 ml of 2 M NaOH (aq), and the reaction was stirred overnight at room temperature. The reaction mixture was concentrated in vacuo, diluted with 5 ml of ethyl acetate and 5 ml of water and acidified to pH 3 with 1N HCl (aq). The organic layer was separated, dried over magnesium sulphate and concentrated in vacuo to give 99 mg of 2-methyl-2-{[1-(4-trifluoromethoxy-benzyloxy)-5,6,7,8-tetrahydro-naphthalene-2-carbonyl]-amino}-propionic acid.

$C_{23}H_{24}F_3NO_5$ (451.16), LCMS (ESI): 452.16 (MH$^+$).

The following examples were prepared in analogy to example 1 via a sequence of an alkylation reaction to attach a suitably substituted alkylating agent to the aromatic hydroxy group of 2-[(1-hydroxy-5,6,7,8-tetrahydro-naphthalene-2-carbonyl)-amino]-2-methyl-propionic acid methyl ester or 2-[(1-hydroxy-5,6,7,8-tetrahydro-naphthalene-2-carbonyl)-amino]-2-methyl-butyric acid methyl ester and a basic hydrolysis of the amino acid ester to the free amino acid:

| Example No. | Structure | Chemical Name | ESI+ or ESI− |
|---|---|---|---|
| 2 | 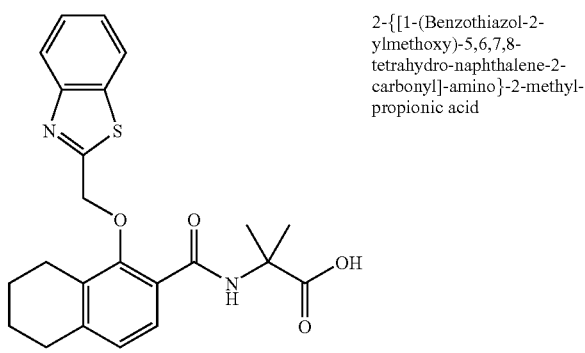 | 2-{[1-(Benzothiazol-2-ylmethoxy)-5,6,7,8-tetrahydro-naphthalene-2-carbonyl]-amino}-2-methyl-propionic acid | 425.14 |

-continued

| Example No. | Structure | Chemical Name | ESI+ or ESI− |
|---|---|---|---|
| 3 | 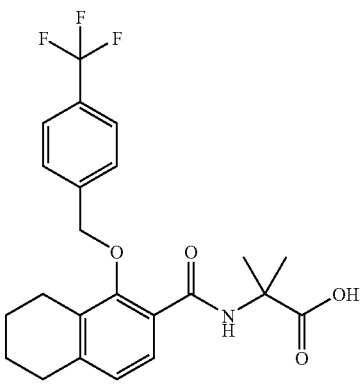 [SMILES: CC(C)(NC(=O)c1ccc2c(c1OCc1ccc(C(F)(F)F)cc1)CCCC2)C(=O)O] | 2-Methyl-2-{[1-(4-trifluoromethyl-benzyloxy)-5,6,7,8-tetrahydro-naphthalene-2-carbonyl]-amino}-propionic acid | 436.16 |
| 4 | 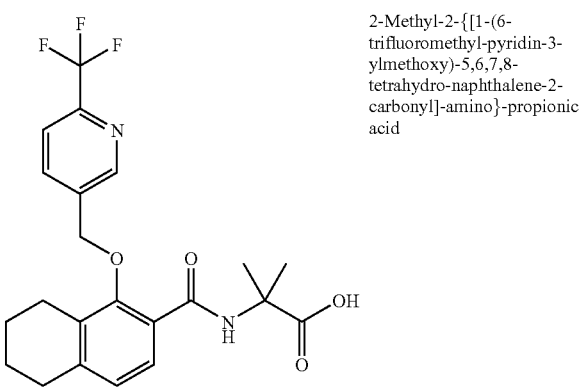 | 2-Methyl-2-{[1-(6-trifluoromethyl-pyridin-3-ylmethoxy)-5,6,7,8-tetrahydro-naphthalene-2-carbonyl]-amino}-propionic acid | 437.17 |
| 5 | 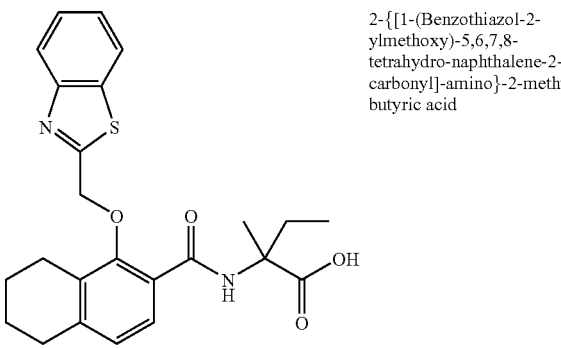 | 2-{[1-(Benzothiazol-2-ylmethoxy)-5,6,7,8-tetrahydro-naphthalene-2-carbonyl]-amino}-2-methyl-butyric acid | 439.19 |
| 6 | 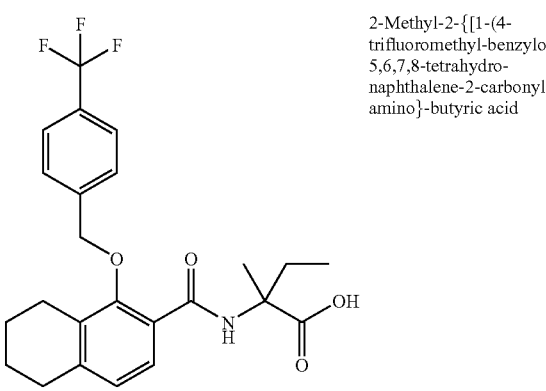 | 2-Methyl-2-{[1-(4-trifluoromethyl-benzyloxy)-5,6,7,8-tetrahydro-naphthalene-2-carbonyl]-amino}-butyric acid | 450.19 |

-continued

| Example No. | Structure | Chemical Name | ESI+ or ESI− |
|---|---|---|---|
| 7 | 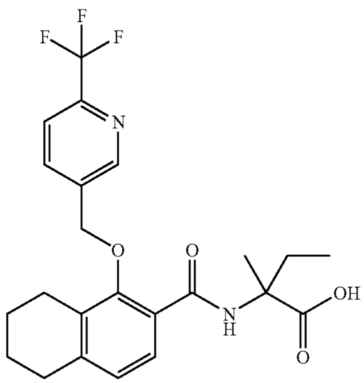 [SMILES: CCC(C)(NC(=O)c1ccc2c(c1OCc1ccc(C(F)(F)F)nc1)CCCC2)C(=O)O] | 2-Methyl-2-{[1-(6-trifluoromethyl-pyridin-3-ylmethoxy)-5,6,7,8-tetrahydro-naphthalene-2-carbonyl]-amino}-butyric acid | 451.17 |
| 8 | 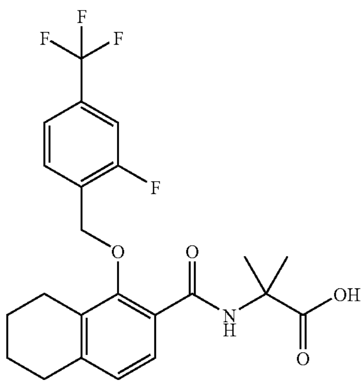 [SMILES: CC(C)(NC(=O)c1ccc2c(c1OCc1ccc(C(F)(F)F)cc1F)CCCC2)C(=O)O] | 2-{[1-(2-Fluoro-4-trifluoromethyl-benzyloxy)-5,6,7,8-tetrahydro-naphthalene-2-carbonyl]-amino}-2-methyl-propionic acid | 454.16 |
| 9 | 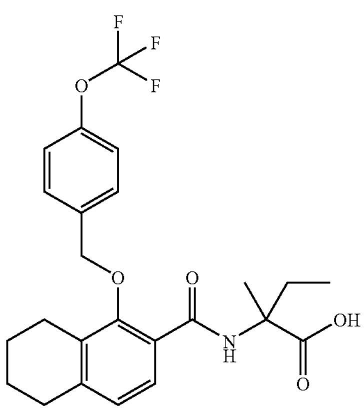 [SMILES: CCC(C)(NC(=O)c1ccc2c(c1OCc1ccc(OC(F)(F)F)cc1)CCCC2)C(=O)O] | 2-Methyl-2-{[1-(4-trifluoromethoxy-benzyloxy)-5,6,7,8-tetrahydro-naphthalene-2-carbonyl]-amino}-butyric acid | 466.20 |
| 10 | 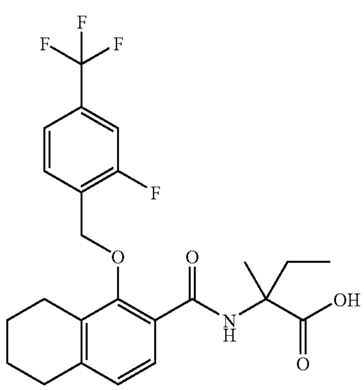 [SMILES: CCC(C)(NC(=O)c1ccc2c(c1OCc1ccc(C(F)(F)F)cc1F)CCCC2)C(=O)O] | 2-{[1-(2-Fluoro-4-trifluoromethyl-benzyloxy)-5,6,7,8-tetrahydro-naphthalene-2-carbonyl]-amino}-2-methyl-butyric acid | 468.18 |

EXAMPLE 11

2-Methyl-2-{[7-methyl-4-(4-trifluoromethyl-benzyloxy)-indane-5-carbonyl]-amino}-propionic acid

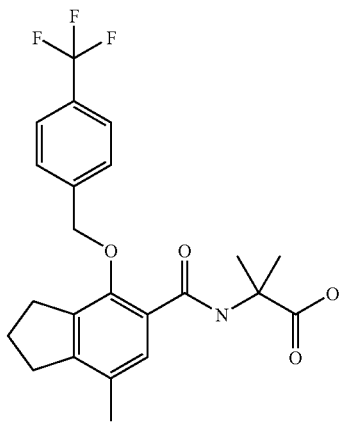 [SMILES: Cc1cc(C(=O)NC(C)(C)C(=O)O)c(OCc2ccc(C(F)(F)F)cc2)c2c1CCC2]

2-Methyl-2-{[7-methyl-4-(4-trifluoromethyl-benzyloxy)-indane-5-carbonyl]-amino}-propionic acid was prepared in analogy to example 1 via a sequence of an alkylation reaction of 2-[(4-Hydroxy-7-methyl-indane-5-carbonyl)-amino]-2-methyl-propionic acid methyl ester using 1-bromomethyl-4-trifluoromethyl-benzene and a basic hydrolysis of the amino acid ester to the free amino acid $C_{23}H_{24}F_3NO_4S$ (435.45), LCMS (ESI): 436.18 (MH$^+$).

EXAMPLE 12

2-Methyl-2-{[7-(4-trifluoromethyl-benzyloxy)-benzo[b]thiophene-6-carbonyl]-amino}-propionic acid

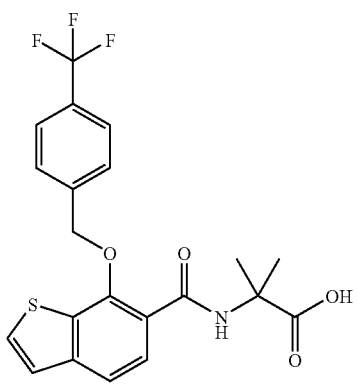 [SMILES: CC(C)(NC(=O)c1ccc2ccsc2c1OCc1ccc(C(F)(F)F)cc1)C(=O)O]

a) 7-(4-Trifluoromethyl-benzyloxy)-benzo[b]thiophene-6-carboxylic acid methyl ester 200 mg 7-Hydroxy-benzo[b]thiophene-6-carboxylic acid methyl ester, 313 mg cesium carbonate, 230 mg of 1-bromomethyl-4-trifluoromethyl-benzene and 32 mg potassium iodide were dissolved in 1 ml of N,N-dimethylformamide and stirred for 3 h at 60° C. 10 ml of ethyl acetate and 10 ml of brine were added to the reaction. The organic layer was separated and washed again with 10 ml of brine. It was then dried over sodium sulphate, filtered and concentrated in vacuo to afford 325 mg of 7-(4-trifluoromethyl-benzyloxy)-benzo[b]thiophene-6-carboxylic acid methyl ester.

$C_{18}H_{13}F_3O_3S$ (366.36), LCMS (ESI): 367.04 (MH$^+$).

b) 7-(4-Trifluoromethyl-benzyloxy)-benzo[b]thiophene-6-carboxylic acid 323 mg 7-(4-Trifluoromethyl-benzyloxy)-benzo[b]thiophene-6-carboxylic acid methyl ester was dissolved in 10 ml of 1,4-dioxane. To this was added 4.4 ml of 1 M LiOH (aq), and the reaction was stirred for 7 h at 60° C. and overnight at room temperature. The reaction mixture was diluted with 5 ml of ethyl acetate, acidified to pH 3 with 2N HCl (aq) and extracted with 10 ml ethyl acetate 4 times. The combined organic layers were washed with brine, dried over sodium sulphate and concentrated in vacuo to give 271 mg of 7-(4-trifluoromethyl-benzyloxy)-benzo[b]thiophene-6-carboxylic acid.

$C_{17}H_{11}F_3O_3S$ (352.33), LCMS (ESI): 353.02 (MH$^+$).

c) 2-Methyl-2-{[7-(4-trifluoromethyl-benzyloxy)-benzo[b]thiophene-6-carbonyl]-amino}-propionic acid methyl ester To a solution of 270 mg 7-(4-Trifluoromethyl-benzyloxy)-benzo[b]thiophene-6-carboxylic acid in 1.5 ml dry dichloromethane was added a drop of N,N-dimethylformamide and 1.15 ml of oxalyl chloride. After stirring for 0.5 h at room temperature, the reaction mixture was evaporated, treated with more dichloromethane and evaporated again. The residue was then taken up in 2 ml of dichloromethane and at 0° C. added to a mixture of 118 mg 2-amino-2-methyl-propionic acid methyl ester hydrochloride in 5 ml ethyl acetate and 5 ml sat. sodium hydrogen carbonate solution. After 2 h the organic phase was separated and the aqueous phase was extracted with ethyl acetate three times. The combined organic layers were washed with 2 N hydrochloric acid, sat. sodium hydrogen carbonate solution and brine, dried over sodium sulphate, and evaporated. The resulting residue was purified by flash chromatography (silica, heptane/ethyl acetate) to yield 308 mg of 2-methyl-2-{[7-(4-trifluoromethyl-benzyloxy)-benzo[b]thiophene-6-carbonyl]-amino}-propionic acid methyl ester.

$C_{22}H_{20}F_3NO_4S$ (451.47), LCMS (ESI): 452.08 (MH$^+$).

d) 2-Methyl-2-{[7-(4-trifluoromethyl-benzyloxy)-benzo[b]thiophene-6-carbonyl]-amino}-propionic acid 308 mg 2-methyl-2-{[7-(4-trifluoromethyl-benzyloxy)-benzo[b]thiophene-6-carbonyl]-amino}-propionic acid methyl ester was dissolved in 5 ml of 1,4-dioxane. To this was added 3.4 ml of 1 M LiOH (aq), and the reaction was stirred for 1 h at 60° C. and overnight at room temperature. The reaction mixture was diluted with 10 ml of ethyl acetate, acidified to pH 3 with 2N HCl (aq) and extracted with 10 ml ethyl acetate four times. The combined organic layers were washed with brine, dried over sodium sulphate and concentrated in vacuo to give 299 mg of 2-methyl-2-{[7-(4-trifluoromethyl-benzyloxy)-benzo[b]thiophene-6-carbonyl]-amino}-propionic acid.

$C_{21}H_{18}F_3NO_4S$ (437.44), LCMS (ESI): 438.09 (MH$^+$).

EXAMPLE 13

2-Methyl-2-{[4-(4-trifluoromethyl-benzyloxy)-benzo[b]thiophene-5-carbonyl]-amino}-propionic acid

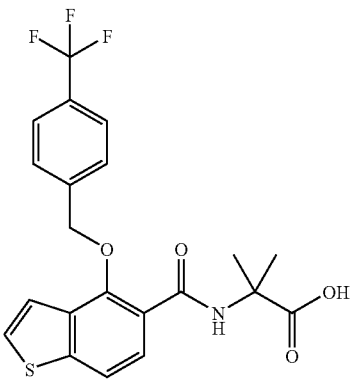 [SMILES: CC(C)(NC(=O)c1ccc2sccc2c1OCc1ccc(C(F)(F)F)cc1)C(=O)O]

a) 2-[(4-Hydroxy-benzo[b]thiophene-5-carbonyl)-amino]-2-methyl-propionic acid tert-butyl ester To a solution of 300 mg 4-Hydroxy-benzo[b]thiophene-5-carboxylic acid in 5 ml N,N-dimethylformamide were added 42 mg 1-hydroxy-benzotriaziole and 285 mg 2-amino-2-methyl-propionic acid tert-butyl ester hydrochloride. At 0° C. 0.77 ml (600 mg) ethyl-diisopropyl-amine and 444 mg (3-dimethylamino-propyl)-ethyl-carbodiimide hydrochloride were added. After 16 h at room temperature 0.51 ml (400 mg) ethyl-diisopropyl-amine and 444 mg (3-dimethylamino-propyl)-ethyl-carbodiimide hydrochloride were added, and after additional 16 h the reaction was diluted with ethyl acetate and washed with brine. The organic layer was dried over magnesium sulphate and concentrated. The resulting residue was purified by flash chromatography (silica, heptane/ethyl acetate) to afford 315 mg 2-[(4-hydroxy-benzo[b]thiophene-5-carbonyl)-amino]-2-methyl-propionic acid tert-butyl ester.

$C_{17}H_{21}NO_4S$ (335.43), LCMS (ESI): 336.20 (MH$^+$), 280.11 (MH$^+$-tBu).

b) 2-Methyl-2-{[4-(4-trifluoromethyl-benzyloxy)-benzo[b]thiophene-5-carbonyl]-amino}-propionic acid tert-butyl ester 80 mg 2-[(4-Hydroxy-benzo[b]thiophene-5-carbonyl)-amino]-2-methyl-propionic acid tert-butyl ester, 90 mg cesium carbonate, 55 mg of 1-bromomethyl-4-trifluoromethyl-benzene and 8 mg potassium iodide were dissolved in 1 ml of N,N-dimethylformamide and stirred for 1 h at 60° C. 10 ml of ethyl acetate and 10 ml of brine were added to the reaction. The organic layer was separated and washed again with 10 ml of brine. It was then dried over sodium sulphate, filtered and concentrated in vacuo. The resulting residue was purified by flash chromatography (silica, heptane/ethyl acetate) to afford 113 mg of 2-methyl-2-{[4-(4-trifluoromethyl-benzyloxy)-benzo[b]thiophene-5-carbonyl]-amino}-propionic acid tert-butyl ester $C_{25}H_{26}F_3NO_4S$ (493.55), LCMS (ESI): 494.30 (MH$^+$).

c) 2-Methyl-2-{[4-(4-trifluoromethyl-benzyloxy)-benzo[b]thiophene-5-carbonyl]-amino}-propionic acid 113 mg of 2-Methyl-2-{[4-(4-trifluoromethyl-benzyloxy)-benzo[b]thiophene-5-carbonyl]-amino}-propionic acid tert-butyl ester were dissolved in 2 ml dichloromethane and treated with 2 ml trifluoroacetic acid. After 30 min at 60° C. the volatiles were evaporated. The residue was treated with ethanol and 2 M HCl and evaporated three times. The resulting residue was crystallized from diethylether/heptane to afford 65 mg of 2-Methyl-2-{[4-(4-trifluoromethyl-benzyloxy)-benzo[b]thiophene-5-carbonyl]-amino}-propionic acid.

$C_{21}H_{18}F_3NO_4S$ (337.44), LCMS (ESI): 438.18 (MH$^+$).

EXAMPLE 14

2-Methyl-2-{[4-(5-trifluoromethyl-pyridin-2-yl-methoxy)-benzo[b]thiophene-5-carbonyl]-amino}-propionic acid

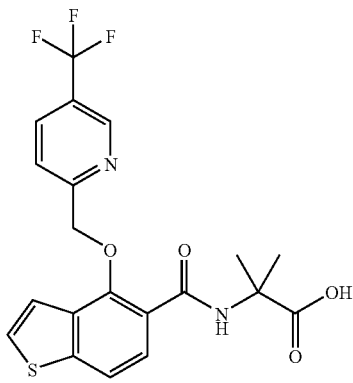 [SMILES: CC(C)(NC(=O)c1ccc2sccc2c1OCc1ccc(C(F)(F)F)cn1)C(=O)O]

2-Methyl-2-{[4-(5-trifluoromethyl-pyridin-2-yl-methoxy)-benzo[b]thiophene-5-carbonyl]-amino}-propionic acid was prepared in analogy to example 13 via a sequence of an alkylation reaction of 2-[(4-Hydroxy-benzo[b]thiophene-5-carbonyl)-amino]-2-methyl-propionic acid tert-butyl ester using 2-bromomethyl-5-trifluoromethyl-pyridine and an acidic hydrolysis of the amino acid ester to the free amino acid $C_{20}H_{17}F_3N_2O_4S$ (438.43), LCMS (ESI): 439.18 (MH$^+$).

Preparation of Intermediates:

2-[(1-Hydroxy-5,6,7,8-tetrahydro-naphthalene-2-carbonyl)-amino]-2-methyl-propionic acid methyl ester

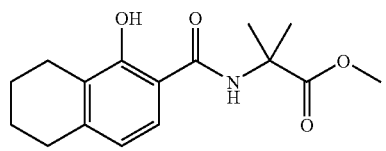 [SMILES: COC(=O)C(C)(C)NC(=O)c1ccc2c(c1O)CCCC2]

a) 5-Methoxymethoxy-1,2,3,4-tetrahydro-naphthalene 1.0 g 5,6,7,8-tetrahydro-naphthalen-1-ol was dissolved in 20 ml of N,N-dimethylformamide. To this solution was added slowly 0.256 g of 95% NaH, followed by addition of 0.768 ml of chloromethoxymethane. The reaction was flushed with nitrogen and left stirring overnight at room temperature. The reaction mixture was then diluted with 50 ml of water and extracted with 50 ml of diethyl ether. The organic layer was washed with 50 ml of water, dried over magnesium sulphate and concentrated in vacuo to afford a crude oil. This was purified by flash chromatography (silica, heptanes/dichloromethane) to afford 1.0 g of 5-methoxymethoxy-1,2,3,4-tetrahydro-naphthalene.

$C_{12}H_{16}O_2$ (192.11), LCMS (ESI): 161.1 ($M^+$-OMe)

b) 1-Methoxymethoxy-5,6,7,8-tetrahydro-naphthalene-2-carboxylic acid

In a small round bottom flask was placed 0.2 g 5-methoxymethoxy-1,2,3,4-tetrahydro-naphthalene in 3 ml of anhydrous diethyl ether. This was cooled to 0 C and flushed with nitrogen. Next, 0.98 ml of 1.6 M nbutyl-lithium was added by syringe followed by 0.156 ml of N,N,N',N'-tetramethylethylenediamine. The reaction was left stirring at 0 C for 1 h, after which it was cooled to −78 C and gaseous carbon dioxide was bubbled through for 15 min. The white suspension formed was warmed up to room temperature slowly and to it was added 10 ml of diethyl ether. The product was extracted with 20 ml of 1M NaOH (aq.) and the aqueous layer was then acidified with $NaHSO_3$ to pH 2 and extracted twice with 20 ml of diethyl ether. The combined organic layers were dried over magnesium sulphate, filtered and concentrated in vacuo to give 0.21 g of 1-methoxymethoxy-5,6,7,8-tetrahydro-naphthalene-2-carboxylic acid.

$C_{13}H_{16}O_4$ (236.27) LC/MS (ESI) observed 259.0 ($M+Na^+$)

c) 2-[(1-Methoxymethoxy-5,6,7,8-tetrahydro-naphthalene-2-carbonyl)-amino]-2-methyl-propionic acid methyl ester In a round bottom flask was placed 0.96 g 1-methoxymethoxy-5,6,7,8-tetrahydro-naphthalene-2-carboxylic acid, 1.25 g 2-amino-2-methyl-propionic acid methyl ester hydrochloride, 3.09 g of O-(7-azabenzotriazole-1-yl)-N,N,N,N-tetramethyluronium hexafluoro phosphate and 2.83 ml of N,N-diisopropylethylamine in 60 ml of N,N-di-methylformamide. It was left stirring at room temperature overnight. 60 ml of diethylether and 60 ml of water were added to the reaction. The organic layer was separated and washed again with 50 ml of water. It was dried over magnesium sulphate, filtered and concentrated in vacuo to afford a crude yellow oil. Purification was performed by flash chromatography (silica, heptanes/ethyl acetate) to give 1.04 g 2-[(1-methoxymethoxy-5,6,7,8-tetrahydro-naphthalene-2-carbonyl)-amino]-2-methyl-propionic acid methyl ester.

$C_{18}H_{25}NO_5$ (335.17) LC/MS (ESI) observed 336.19 (M+H).

d) 2-[(1-Hydroxy-5,6,7,8-tetrahydro-naphthalene-2-carbonyl)-amino]-2-methyl-propionic acid methyl ester 1.023 g 2-[(1-methoxymethoxy-5,6,7,8-tetrahydro-naphthalene-2-carbonyl)-amino]-2-methyl-propionic acid methyl ester was dissolved in a mixture of isopropanol (8 ml), tetrahydrofurane (8 ml) and HCl conc. (4 ml). It was stirred at room temperature for one hour. The mixture was concentrated in vacuo, then 20 ml of ethyl acetate and 30 ml of water were added to the residue. The organic layer was separated, dried over magnesium sulphate and concentrated in vacuo to afford 0.857 g of 2-[(1-hydroxy-5,6,7,8-tetrahydro-naphthalene-2-carbonyl)-amino]-2-methyl-propionic acid methyl ester.

$C_{16}H_{21}NO_4$ (291.15), LC/MS (ESI) 292.15 (M+H)

2-[(1-Hydroxy-5,6,7,8-tetrahydro-naphthalene-2-carbonyl)-amino]-2-methyl-butyric acid methyl ester

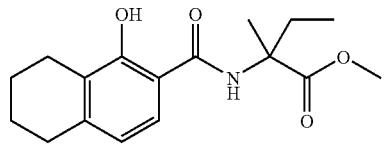 [SMILES: CCC(C)(NC(=O)c1ccc2c(c1O)CCCC2)C(=O)OC]

2-[(1-Hydroxy-5,6,7,8-tetrahydro-naphthalene-2-carbonyl)-amino]-2-methyl-butyric acid methyl ester was prepared in analogy to 2-[(1-hydroxy-5,6,7,8-tetrahydro-naphthalene-2-carbonyl)-amino]-2-methyl-propionic acid methyl ester.

$C_{17}H_{23}NO_4$ (305.38), LC/MS (ESI) 306.15 (M+H)

2-[(4-Hydroxy-7-methyl-indane-5-carbonyl)-amino]-2-methyl-propionic acid methyl ester

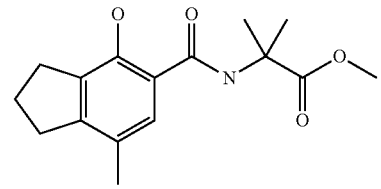 [SMILES: COC(=O)C(C)(C)NC(=O)c1cc(C)c2c(c1O)CCC2]

2-[(4-Hydroxy-7-methyl-indane-5-carbonyl)-amino]-2-methyl-propionic acid methyl ester was prepared in analogy to 2-[(1-hydroxy-5,6,7,8-tetrahydro-naphthalene-2-carbonyl)-amino]-2-methyl-propionic acid methyl ester.

$C_{16}H_{21}NO_4$ (291.35), LC/MS (ESI) 292.15 (M+H)

Determination of CXCR2 Inhibition: Calcium Fluorescence Assay (FLIPR)

The assay is based on the detection of intracellular calcium changes detected by the selective, calcium-chelating dye, Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. Hence, influx of calcium to this cytoplasmic pocket, via release from intracellular pools and the phospholipase C cascade can be detected. By co-expressing the CXCR2 receptor and the promiscuous $G_{\alpha 16}$ protein, activation of this chemokine receptor is directed into this phospholipase C cascade resulting in intracellular calcium mobilization.

The CHO-K1 cells stably transfected with human CXCR2 and the promiscuous $G_{\alpha 16}$ protein were maintained in a log phase of growth at 37° C. and 5% $CO_2$ in the following media: Iscove's, 10% FBS, 1× Penicillin-Streptomycin, 400 μg/ml G418 and 350 μg/ml Zeocin. Approximately 24-48 hours prior to the assay, 20,000-30,000 cells/well were plated onto a 96-well black/clear bottomed assay plate (Becton Dickinson) with a well volume of 180 μl. For dye loading the culture medium was carefully removed and replaced by 100 μl/well dye solution (4 μM Fluo-4 in 135 mM NaCl, 5 mM KCl, 1 mM magnesium sulphate, 5 mM glucose, 20 mM hepes, 2.5 mM probenecid; pH 7.4). Cells were incubated for 1 h at 37° C., and then washed 3× with buffer. After washing 90 μl buffer/well were left. Increasing concentrations of compound was added in 45 μl buffer (4× concentrated) followed by 10 min incubation at 37° C. Then the chemokine (10-100 nM) was applied in 45 μl buffer (4× concentrated) and the measurement performed for 2 min. The IC50 value of a compound was determined by calculation of % inhibition of total calcium response to the chemokine.

Compounds of this invention exhibit activity in the CXCR2-calcium fluorescence (FLIPR) assay in a range of about 0.01 nM to 30000 nM. Some compounds of the invention may additionally exhibit activity as modulators of CXCR1 and CX3CR1.

CXCR2 inhibition with chemokine IL-8 for selected example compounds:

| Example No. | IC50 [μM] |
|---|---|
| 2 | 0.6 |
| 5 | 0.4 |
| 8 | 1.8 |
| 9 | 1.5 |
| 11 | 1.6 |
| 12 | 0.7 |
| 13 | 1.1 |

The invention claimed is:
1. A compound of the formula I

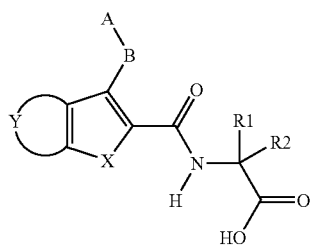

wherein
X is —CR3=CR4-, NR7-, or —S—;
wherein R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO$_2$, NR27R28, C(O)R29, C(O)NR30R31, S(O)$_o$R32, S(O)$_p$NR33R34, aryl, heteroaryl, arylalkyl with alkyl having 1, 2, 3 or 4 carbon atoms or heteroarylalkyl with alkyl having 1, 2, 3 or 4 carbon atoms;
wherein
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34 are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p are, independently of one another, 1 or 2; and
R7 is hydrogen, alkyl having 1, 2, 3 or 4 carbon atoms or C(O)R35;
R35 is hydrogen, alkyl with 1, 2, 3 or 4 carbon atoms or aryl;
Y is —C(R61R62)-C(R61R62)-C(R61R62)-,
—S(O)$_u$—C(R63R64)-C(R61R62)-,
—C(R63R64)-S(O)$_u$—C(R63R64)-,
—C(R61R62)-C(R63R64)-S(O)$_u$—
—C(R61R62)-C(R61R62)-C(R61R62)-C(R61R62)-,
—S(O)$_u$—C(R63R64)-C(R61R62)-C(R61R62)-,
—C(R63R64)-S(O)$_u$—C(R63R64)-C(R61R62)-,
—C(R61R62)-C(R63R64)-S(O)$_u$—C(R63R64)-,
—C(R61R62)-C(R61R62)-C(R63R64)-S(O)$_u$—,
—S(O)$_u$—C(R63R64)-C(R63R64)-S(O)$_u$—,
—S(O)$_v$—CR65=CR66- or
—CR67=CR68-S(O)$_v$—;
wherein R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or SCF$_3$;
R62, R63 and R64 are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$;

u is 0, 1 or 2; and v is 0, 1 or 2;

A is cycloalkyl having 3, 4, 5, 6, 7 or 8 carbon atoms, heterocycle, aryl or heteroaryl;

in which the cycloalkyl or heterocycle radical can be condensed to an aryl or heteroaryl radical and in which the cycloalkyl or heterocycle radical and the optionally condensed aryl or heteroaryl radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl and —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—(CH$_2$)$_b$—(CF$_2$)$_c$—CF$_3$;

wherein R9 is hydrogen or alkyl having 1, 2, 3 or 4 carbon atoms,

R10 is hydrogen, alkyl having 1, 2, 3 or 4 carbon atoms, aryl, C(O)H, C(O) alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49 are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l are, independently of one another, zero, 1, 2 or 3; and s and t are, independently of one another, 1 or 2;

and in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl and —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—(CH$_2$)$_b$—(CF$_2$)$_c$—CF$_3$;

wherein R9 is hydrogen or alkyl having 1, 2, 3 or 4 carbon atoms;

R10 is hydrogen, alkyl having 1, 2, 3 or 4 carbon atoms, aryl, C(O)H, C(O) alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49 are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l are, independently of one another, zero, 1, 2 or 3; and s and t are, independently of one another, 1 or 2;

B is —O—C(R11R12)-, —C(R50R51)-O—, —C≡C—, —CR52=CR53-, —C(R13R14)-C(R15R16)-, —NR17-C(R18R19)-, —C(R54R55)—NR56-, —NR20-C(O)— or —C(O)—NR57-;

wherein R11, R12, R13, R14, R15, R16, R17, R18, R19, R20, R50, R51, R52, R53, R54, R55, R56 and R57 are, independently of one another, hydrogen or alkyl having 1, 2, 3 or 4 carbon atoms, in which 1, 2, 3, 4, 5, 6, 7, 8 or 9 hydrogen atoms may be substituted by fluorine atoms;

R1 is hydrogen or alkyl having 1, 2, 3, 4, 5 or 6 carbon atoms;

which can be unsubstituted or substituted by 1, 2, 3, 4 or 5 radicals selected from the group consisting of F, Cl, Br, I, and —O$_i$—(CH$_2$)$_j$—R25;

wherein i is 0 or 1;

j is 0, 1, 2 or 3; and

R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4 5, 6, 7 or 8 atoms;

wherein alkyl is unsubstituted or substituted by 1, 2, 3, 4 or 5 radicals selected from the group consisting of F, Cl, Br, I, and —O$_m$—(CH$_2$)$_n$—R26;

wherein m is 0, or 1;

n is 0, 1, 2 or 3; and

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2, or 3 radicals selected from the group consisting of F, Cl, Br and I;

and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; or R1 and R2 form, together with the carbon atom to which they are attached, a 3-, 4-, 5- or 6-membered carbon ring, wherein one carbon atom, which is not adjacent to the carbon atom, to which R1 and R2 are attached, can be replaced by —O—, —NR58- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein the formed ring and the condensed phenyl, heteroaryl, cycloalkyl or heterocyclyl radical can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl; and w is 0, 1 or 2;

or a pharmaceutically acceptable salt thereof.

2. A compound of formula I as claimed in claim 1, wherein:
X is —CR3=CR4-, —NR7-, or —S—;
wherein R3 and R4 are, independently of one another, hydrogen, F, Cl, Br, I, alkyl having 1, 2, 3 or 4 carbon atoms or alkoxy having 1, 2, 3 or 4 carbon atoms; and
R7 is hydrogen or alkyl having 1, 2, 3 or 4 carbon atoms;
Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;

wherein R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;

R62, R63 and R64 are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso, that in any embodiment of Y a maximum of 4 of the substituents R61 to R64 are not hydrogen; and R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$;

A is cycloalkyl having 3, 4, 5, 6, 7 or 8 carbon atoms, heterocycle, aryl or heteroaryl;

in which the cycloalkyl or heterocycle radical can be condensed to an aryl radical and in which the cycloalkyl or heterocycle radical is unsubstituted or substituted by 1, 2 or 3 radicals selected from the group consisting of F, Cl, Br, I, alkyl having 1, 2, 3 or 4 carbon atoms, —C(O)-alkyl having 1, 2, 3 or 4 carbon atoms, —C(O)-cycloalkyl having 3, 4, 5 or 6 carbon atoms and —C(O)O-alkyl having 1, 2, 3 or 4 carbon atoms;

in which the aryl or heteroaryl radical can be condensed to an cycloalkyl or heterocycle radical and in which the aryl or heteroaryl radical is unsubstituted or substituted by 1, 2, 3 or 4 radicals selected from the group consisting of F, Cl, Br, I, CN, $NO_2$, $SF_5$, —NR9R10, alkoxy having 1, 2, 3 or 4 carbon atoms, alkyl having 1, 2, 3, 4, 5 or 6 carbon atoms, —$O_a$—$(CH_2)_b$—$(CF_2)_c$—$CF_3$, —$O_d$—$CHF_2$, —$O_e$—$CH_2F$, —$SO_f$-alkyl having 1, 2, 3 or 4 carbon atoms, S—$(CH_2)_g$—$(CF_2)_h$—$CF_3$, —$(CH_2)_k$-aryl and —$(CH_2)_l$-heteroaryl, in which the aryl and heteroaryl radicals can be substituted by F, Cl, Br, I, $CF_3$, alkoxy having 1, 2, 3 or 4 carbon atoms or alkyl having 1, 2, 3 or 4 carbon atoms;

wherein R9 and R10 are, independently of one another, hydrogen or alkyl having 1, 2, 3 or 4 carbon atoms;

a, d and e are, independently of one another, zero or 1;

b, c, g, h, k and l are, independently of one another, zero, 1, 2 or 3; and f is zero, 1 or 2;

B is —O—(CR11R12)-, —C≡C—, —C(R13R14)-C(R15R16)-, —NR17-C(R18R19)- or —NR20-C(O)—;
wherein R11, R12, R13, R14, R15, R16, R17, R18, R19 and R20 are, independently of one another, hydrogen or alkyl having 1, 2, 3 or 4 carbon atoms;
R1 is hydrogen or alkyl having 1, 2, 3, 4, 5 or 6 carbon atoms; and
R2 is alkyl having 1, 2, 3, 4, 5 or 6 carbon atoms or phenyl;
wherein alkyl is unsubstituted or substituted by 1, 2, 3, 4 or 5 radicals selected from the group consisting of F, Cl, Br, I, and —$O_m$—$(CH_2)_n$—R26;
wherein m is 0, or 1;
n is 0, 1, 2 or 3; and
R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2, or 3 radicals selected from the group consisting of F, Cl, Br and I; or
R1 and R2 form, together with the carbon atom to which they are attached, a 3-, 4, 5- or 6-membered saturated or partly saturated carbon ring, which can be condensed to phenyl; or
R1 and R2 form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NH—or —S—;
or a pharmaceutically acceptable salt thereof.

3. A compound of the formula I as claimed in claim 1, wherein

X is —CR3=CR4-, —NH—, or —S—;
wherein R3 and R4 are, independently of one another, hydrogen, F, Cl, Br or alkyl having 1, 2, 3, or 4 carbon atoms;
Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;
R61, R62, R63 and R64 are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
with the proviso, that in any embodiment of Y a maximum of 4 of the substituents R61 to R64 are not hydrogen; and
R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
A is cyclohexyl or an aryl or heteroaryl radical selected from the group consisting of phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl and quinolyl;
in which the cyclohexyl is unsubstituted or substituted by 1, 2 or 3 radicals selected from the group consisting of F and alkyl having 1, 2, 3 or 4 carbon atoms;
in which the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, —$CF_3$, —$OCF_3$, —$OCH_2CF_3$, —$OCHF_2$, —$SCH_3$—, —$SOCH_3$, —$SO_2CH_3$, —$SCF_3$, phenyl and benzyl; wherein phenyl can be substituted by Cl;
B is —O—C(R11R12)-; —C≡C—, or —C(R13R14)-C(R15R16)-;
R11, R13, R14, R15 and R16 are hydrogen;
R12 is hydrogen or methyl;
R1 is alkyl having 1, 2, 3 or 4 carbon atoms; and
R2 is alkyl having 1, 2, 3 or 4 carbon atoms, phenyl or benzyl; or
R1 and R2 form, together with the carbon atom to which they are attached, a cyclopropane, cyclobutane, cyclopentane, cyclohexane, cyclopentene ring or indene; or
R1 and R2 form, together with the carbon atom to which they are attached, a tetrahydro-thiophene or tetrahydro-thiopyrane ring;
or a pharmaceutically acceptable salt thereof.

4. A compound of the formula I as claimed in claim 1, wherein

X is —CR3=CR4- or —S—;
wherein R3 and R4 are, independently of one another, hydrogen, F, Cl, Br or alkyl having 1, 2, 3, or 4 carbon atoms;
Y is —C(R61R62)-C(R61R62)-C(R61R62)-,
—C(R61R62)-C(R61R62)-C(R61R62)-C(R61R62)-,
—S—CR65=CR66- or
—CR67=CR68-S—;
wherein R61 and R62 are, independently of one another, hydrogen, F or alkyl having 1, 2, 3 or 4 carbon atoms;
with the proviso, that in any embodiment of Y a maximum of 4 of the substituents R61 to R62 are not hydrogen; and
R65, R66, R67 and R68 are, independently of one another, hydrogen, F, Cl, Br, I or alkyl having 1, 2, 3 or 4 carbon atoms;
A is cyclohexyl or an aryl or heteroaryl radical selected from the group consisting of phenyl, naphthyl, indanyl, thienyl, pyridyl, thiazolyl, pyrazinyl, pyrimidinyl, pyridazinyl, benzothiophenyl, benzothiazolyl and quinolyl;
wherein cyclohexyl is unsubstituted or substituted by 1, 2 or 3 radicals selected from the group consisting of F and alkyl having 1, 2, 3 or 4 carbon atoms,
and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl;
B is —O—C(R11R12)-;
wherein R11 is hydrogen; and
R12 is hydrogen or methyl;
R1 is methyl or ethyl; and
R2 is methyl or ethyl; or
R1 and R2 form, together with the carbon atom to which they are attached, a cyclobutane or cyclopentane ring;
or a pharmaceutically acceptable salt thereof.

5. A compound of the formula I as claimed in claim 1, wherein:

X is —CR3=CR4-;
wherein R3 and R4 are, independently of one another, hydrogen, F or methyl;

Y is —C(R61R62)-C(R61R62)-C(R61R62)-
or —C(R61R62)-C(R61R62)-C(R61R62)-C(R61R62)-;
wherein R61 and R62 are, independently of one another, hydrogen or F;
with the proviso, that in any embodiment of Y a maximum of 4 of the substituents R61 to R62 are not hydrogen;
A is phenyl, pyridyl or benzothiazolyl; which are unsubstituted or substituted by F, $CF_3$ or $OCF_3$;
B is —O13 $CH_2$-;
R1 is methyl; and
R2 is methyl or ethyl;
or a pharmaceutically acceptable salt thereof.

6. A compound of the formula I as claimed in claim 1 selected from the group consisting of:
2-Methyl-2-{[1-(4-trifluoromethoxy-benzyloxy)-5,6,7,8-tetrahydro-naphthalene-2-carbonyl]-amino}-propionic acid;
2-{[1-(Benzothiazol-2-ylmethoxy)-5,6,7,8-tetrahydro-naphthalene-2-carbonyl]-amino}-2-methyl-propionic acid;
2-Methyl-2-{[1-(4-trifluoromethyl-benzyloxy)-5,6,7,8-tetrahydro-naphthalene-2-carbonyl]-amino}-propionic acid;
2-Methyl-2-{[1-(6-trifluoromethyl-pyridin-3-yl-methoxy)-5,6,7,8-tetrahydro-naphthalene-2-carbonyl]-amino}-propionic acid;
2-{[1-(Benzothiazol-2-ylmethoxy)-5,6,7,8-tetrahydro-naphthalene-2-carbonyl]-amino}-2-methyl-butyric acid;
2-Methyl-2-{[1-(4-trifluoromethyl-benzyloxy)-5,6,7,8-tetrahydro-naphthalene-2-carbonyl]-amino}-butyric acid;
2-Methyl-2-{[1-(6-trifluoromethyl-pyridin-3-yl-methoxy)-5,6,7, 8-tetrahydro-naphthalene-2-carbonyl]-amino}-butyric acid;
2-{[1-(2-Fluoro-4-trifluoromethyl-benzyloxy)-5,6,7,8-tetrahydro-naphthalene-2-carbonyl]-amino}-2-methyl-propionic acid;
2-Methyl-2-{[1 -(4-trifluoromethoxy-benzyloxy)-5,6,7,8-tetrahydro-naphthalene-2-carbonyl]-amino}-butyric acid;
2-{[1-(2-Fluoro-4-trifluoromethyl-benzyloxy)-5,6,7,8-tetrahydro-naphthalene-2-carbonyl]-amino}-2-methyl-butyric acid;
2-Methyl-2-{[7-methyl-4-(4-trifluoromethyl-benzyloxy)-indane-5 -carbonyl]-amino}-propionic acid;
2-Methyl-2-{[7-(4-trifluoromethyl-benzyloxy)-benzo[b]thiophene-6-carbonyl]-amino}-propionic acid;
2-Methyl-2-{[4-(4-trifluoromethyl-benzyloxy)-benzo[b]thiophene-5-carbonyl]-amino}-propionic acid; and
2-Methyl-2-{[4-(5-trifluoromethyl-pyridin-2-yl-methoxy)-benzo[b]thiophene-5-carbonyl]-amino}-propionic acid;
or a pharmaceutically acceptable salt thereof.

7. A compound of the formula I or a pharmaceutically acceptable salt as claimed in claim 1 for use as a medicament.

8. A method for treating a patient afflicted with a chemokine mediated disease selected from atherosclerosis, ischemia/reperfusion injuries, chronic obstructive pulmonary disease, asthma, and rheumatoid arthritis, adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis and cancer, the method comprising administering to said patient an effective amount of a compound of claim 1.

9. A pharmaceutical composition comprising an effective amount of a compound of claim 1 or a pharmaceutically acceptable salt thereof and a pharmaceutically acceptable carrier.

10. A pharmaceutical composition comprising an effective amount of a compound of claim 1 or a pharmaceutically acceptable salt thereof and a pharmaceutically acceptable carrier in combination with at least one other pharmacological active ingredient.

11. The method of claim 8, wherein said chemokine mediated disease is selected from atherosclerosis, ischemia/reperfusion injuries, chronic obstructive pulmonary disease, asthma, and rheumatoid arthritis.

12. The method of claim 8, wherein said chemokine mediated disease is atherosclerosis.

\* \* \* \* \*